United States Patent
Aiki et al.

(10) Patent No.: US 10,328,418 B1
(45) Date of Patent: Jun. 25, 2019

(54) METHOD FOR PRODUCING CATALYST AND METHOD FOR PRODUCING ACRYLONITRILE

(71) Applicant: ASAHI KASEI KABUSHIKI KAISHA, Tokyo (JP)

(72) Inventors: Shota Aiki, Tokyo (JP); Akiyoshi Fukuzawa, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/320,428

(22) PCT Filed: Aug. 1, 2017

(86) PCT No.: PCT/JP2017/027950
§ 371 (c)(1),
(2) Date: Jan. 24, 2019

(87) PCT Pub. No.: WO2018/043007
PCT Pub. Date: Mar. 8, 2018

(30) Foreign Application Priority Data

Aug. 31, 2016 (JP) .................. 2016-169708
Jun. 23, 2017 (JP) .................. 2017-123320

(51) Int. Cl.
| | | |
|---|---|---|
| *B01J 21/08* | (2006.01) | |
| *B01J 37/04* | (2006.01) | |
| *C07C 253/18* | (2006.01) | |
| *B01J 23/887* | (2006.01) | |
| *B01J 37/00* | (2006.01) | |
| *B01J 37/08* | (2006.01) | |

(52) U.S. Cl.
CPC ........... *B01J 23/8878* (2013.01); *B01J 21/08* (2013.01); *B01J 23/8876* (2013.01); *B01J 37/0045* (2013.01); *B01J 37/04* (2013.01); *B01J 37/088* (2013.01); *C07C 253/18* (2013.01)

(58) Field of Classification Search
CPC .... B01J 23/8878; B01J 21/08; B01J 23/8876; B01J 37/0045; B01J 37/04; B01J 37/088; C07C 253/18
USPC ....................................... 558/324
See application file for complete search history.

(56) References Cited

U.S. PATENT DOCUMENTS

| | | |
|---|---|---|
| 4,677,084 A | 6/1987 | Bergna |
| 5,132,269 A | 7/1992 | Sasaki et al. |
| 2004/0106817 A1 | 6/2004 | Paparizos et al. |
| 2008/0200715 A1 | 8/2008 | Lugmair et al. |
| 2009/0075814 A1 | 3/2009 | Duvenhage et al. |
| 2009/0221843 A1 | 9/2009 | Watanabe et al. |
| 2011/0034330 A1 | 2/2011 | Czaja et al. |
| 2013/0027410 A1 | 1/2013 | Ginzburg et al. |

FOREIGN PATENT DOCUMENTS

| | | |
|---|---|---|
| CN | 104874399 A | 9/2015 |
| JP | 62-144752 A | 6/1987 |
| JP | 4-118051 A | 4/1992 |
| JP | 2000-5603 A | 1/2000 |
| JP | 2000-37631 A | 2/2000 |
| JP | 2008-212779 A | 9/2008 |
| JP | 2010-519202 A | 6/2010 |
| JP | 2010-172851 A | 8/2010 |
| JP | 4588533 B2 | 12/2010 |
| JP | 2011-518659 A | 6/2011 |
| JP | 4709549 B2 | 6/2011 |
| JP | 2012-77039 A | 4/2012 |
| JP | 5011167 B2 | 8/2012 |
| JP | 2013-17917 A | 1/2013 |
| JP | 5188005 B2 | 4/2013 |
| JP | 2013-146655 A | 8/2013 |
| JP | 2013-169482 A | 9/2013 |
| JP | 5371692 B2 | 12/2013 |
| JP | 5491037 B2 | 5/2014 |
| JP | 2014-522038 A | 8/2014 |
| JP | 2016-120468 A | 7/2016 |

OTHER PUBLICATIONS

International Search Report (PCT/ISA/210) issued in PCT/JP2017/027950, dated Sep. 12, 2017.
International Preliminary Report on Patentability and English translation of the Written Opinion of the International Searching Authority for International Application No. PCT/JP2017/027950, dated Mar. 5, 2019.

*Primary Examiner* — Kristin A Vajda
(74) *Attorney, Agent, or Firm* — Birch, Stewart, Kolasch & Birch, LLP

(57) ABSTRACT

A method for producing a catalyst according to the present invention includes: a preparation step of preparing a precursor slurry comprising molybdenum, bismuth, iron, silica, and a carboxylic acid; a drying step of spray-drying the precursor slurry and thereby obtaining a dried particle; and a calcination step of calcining the dried particle, wherein the preparation step comprises: a step (I) of mixing a starting material for silica with the carboxylic acid and thereby preparing a silica-carboxylic acid mixed liquid; and a step (II) of mixing the silica-carboxylic acid mixed liquid, molybdenum, bismuth, and iron.

12 Claims, 1 Drawing Sheet

METHOD FOR PRODUCING CATALYST AND METHOD FOR PRODUCING ACRYLONITRILE

TECHNICAL FIELD

The present invention relates to a method for producing a catalyst and a method for producing acrylonitrile.

BACKGROUND ART

A reaction for producing acrylonitrile by reacting propylene with ammonia in the presence of molecular oxygen is known as "ammoxidation reaction", and this reaction is used as a method for industrially producing acrylonitrile.

In this reaction, an oxide catalyst is utilized for achieving a favorable acrylonitrile yield. For example, a catalyst containing Mo—Bi—Fe or Fe—Sb as essential components is industrially used. Catalysts obtained by adding additional elements to the above-described essential components in order to achieve a further favorable acrylonitrile yield are also known (see, for example, Patent Literatures 1 and 2).

On the other hand, attempts to improve the acrylonitrile yield by not only improving a metal composition but also improving a catalyst preparation step have also been made. For example, Patent Literatures 3, 4 and 5 describe a method for preparing an ammoxidation catalyst containing molybdenum, bismuth, and iron as essential components, in which a carboxylic acid is added to a starting material slurry.

CITATION LIST

Patent Literature

Patent Literature 1: Japanese Patent Laid-Open No. 2013-169482
Patent Literature 2: Japanese Patent Laid-Open No. 2008-212779
Patent Literature 3: Japanese Patent Laid-Open No. 2013-17917
Patent Literature 4: Japanese Patent Laid-Open No. 2000-5603
Patent Literature 5: Japanese Patent Laid-Open No. 2000-37631

SUMMARY OF INVENTION

Technical Problem

The catalysts prepared by the methods described in Patent Literatures 3, 4, and 5 have more improved acrylonitrile selectivity than catalysts obtained from a starting material slurry to which a carboxylic acid is not added, but from the viewpoint of industrial use, a satisfactory yield has not necessarily been obtained so far. That is, an ammoxidation catalyst giving a sufficiently high acrylonitrile yield cannot be obtained by the techniques described in Patent Literatures 1 to 5.

The present invention has been completed in consideration of the problems, and an object of the present invention is to provide a method for producing a catalyst exhibiting a high acrylonitrile yield and a method for producing acrylonitrile.

Solution to Problem

The present inventors have conducted studies to solve the problems to find that the problems can be solved by devising the timing of adding a carboxylic acid in a catalyst production step, thereby completed the present invention.

That is, the present invention is as follows.

[1]
A method for producing a catalyst, comprising:
a preparation step of preparing a precursor slurry comprising molybdenum, bismuth, iron, silica, and a carboxylic acid;
a drying step of spray-drying the precursor slurry and thereby obtaining a dried particle; and
a calcination step of calcining the dried particle, wherein the preparation step comprises:
a step (I) of mixing a starting material for silica with the carboxylic acid and thereby preparing a silica-carboxylic acid mixed liquid; and
a step (II) of mixing the silica-carboxylic acid mixed liquid, molybdenum, bismuth, and iron.

[2]
The method for producing the catalyst according to [1], wherein the catalyst comprises:
a metal oxide having a bulk composition represented by the following formula (1); and
silica:

$$Mo_{12}Bi_aFe_bX_cY_dZ_eO_f \qquad (1)$$

wherein X represents at least one element selected from the group consisting of nickel, cobalt, magnesium, calcium, zinc, strontium, and barium; Y represents at least one element selected from the group consisting of cerium, chromium, lanthanum, neodymium, yttrium, praseodymium, samarium, aluminum, gallium, and indium; Z represents at least one element selected from the group consisting of potassium, rubidium, and cesium; a, b, c, d, e and f represent an atomic ratio of each element, and satisfy $0.1 \leq a \leq 3.0$, $0.1 \leq b \leq 3.0$, $0.1 \leq c \leq 10.0$, $0.1 \leq d \leq 3.0$, and $0.01 \leq e \leq 2.0$, respectively, and f represents a number of oxygen atoms needed to satisfy atomic valence requirements of the other elements present therein.

[3]
The method for producing the catalyst according to [2], wherein in the catalyst, a standard deviation of values obtained by dividing a ratio of a molar concentration of Bi to a molar concentration of Mo on a surface of catalyst particles by a ratio of a molar concentration of Bi to a molar concentration of Mo in a metal oxide bulk is 0.2 or less.

[4]
The method for producing the catalyst according to any of [1] to [3], wherein
the step (II) comprises the following (i) step and (ii) step, and
the drying step comprises the following (iii) step;
(i) a step of preparing a Mo-containing liquid comprising at least Mo and a Bi-containing liquid comprising at least Bi,
(ii) a step of continuously supplying the Mo-containing liquid to a first flow channel, continuously supplying the Bi-containing liquid to a second flow channel, and merging the first flow channel and the second flow channel at downstream from both points of supply of the Mo-containing liquid and the Bi-containing liquid, thereby mixing the Mo-containing liquid and the Bi-containing liquid to obtain a MoBi-containing liquid, and
(iii) a step of drying the MoBi-containing liquid.

[5]
The method for producing the catalyst according to [4], further comprising (iv) a step of further mixing the MoBi-containing liquid performed between the (ii) step and the (iii) step.

[6]

The method for producing the catalyst according to [4] or [5], further comprising (v) a step of storing the MoBi-containing liquid performed between the (ii) step and the (iii) step.

[7]

The method for producing the catalyst according to [6], wherein a series of treatments of the (i), (ii), and (v) steps is performed in a batch treatment methodology, and a whole amount of one batch of the MoBi-containing liquid obtained in the (ii) step is stored in the (v) step; and in the (ii) step, when mass supply rates of the Mo-containing liquid and the Bi-containing liquid to the first flow channel and the second flow channel, respectively, are denoted as mA (g/min) and mB (g/min), respectively, 60% by mass or more of a total amount of whole amounts of the Mo-containing liquid and the Bi-containing liquid supplied per batch, MA (g) and MB (g), respectively, is supplied such that the following formula (2) is satisfied:

$$(mB/mA)/(MB/MA)=0.5 \text{ to } 1.5 \quad (2).$$

[8]

The method for producing the catalyst according to [4] or [5], wherein the MoBi-containing liquid is continuously supplied to the (iii) step.

[9]

The method for producing the catalyst according to [4], [5], or [8], wherein in the (ii) step, when molar supply rates of the Mo-containing liquid and the Bi-containing liquid to the first flow channel and the second flow channel, respectively, are denoted as mα (mol/min) and mβ (mol/min), respectively, the Mo-containing liquid and the Bi-containing liquid are supplied such that the following formula (3) is satisfied:

$$(m\beta/m\alpha)/(a/12)=0.8 \text{ to } 1.2 \quad (3).$$

[10]

A method for producing acrylonitrile, comprising:

a step of obtaining the catalyst by the method for producing the catalyst according to any of [1] to [9]; and a step of reacting propylene, molecular oxygen, and ammonia in a presence of the catalyst.

[11]

A catalyst comprising a particle, the particle comprising:

a metal oxide having a bulk composition represented by the following formula (1); and silica, wherein a standard deviation of values obtained by dividing a ratio of a molar concentration of Bi to a molar concentration of Mo on a surface of the catalyst particles by a ratio of a molar concentration of Bi to a molar concentration of Mo in a metal oxide bulk is 0.2 or less:

$$Mo_{12}Bi_aFe_bX_cY_dZ_eO_f \quad (1)$$

wherein X represents at least one element selected from the group consisting of nickel, cobalt, magnesium, calcium, zinc, strontium, and barium; Y represents at least one element selected from the group consisting of cerium, chromium, lanthanum, neodymium, yttrium, praseodymium, samarium, aluminum, gallium, and indium; Z represents at least one element selected from the group consisting of potassium, rubidium, and cesium; a, b, c, d, e and f represent an atomic ratio of each element, and satisfy $0.1 \leq a \leq 3.0$, $0.1 \leq b \leq 3.0$, $0.1 \leq c \leq 10.0$, $0.1 \leq d \leq 3.0$, and $0.01 \leq e \leq 2.0$, respectively, and f represents a value satisfying a balance of atomic valences.

[12]

A method for producing acrylonitrile, comprising a step of reacting propylene, molecular oxygen, and ammonia in the presence of the catalyst according to [11].

Advantageous Effects of Invention

According to the present invention, a catalyst and a method for producing a catalyst each giving an excellent acrylonitrile yield, and a method for producing acrylonitrile can be provided.

DESCRIPTION OF EMBODIMENTS

Figure 1:
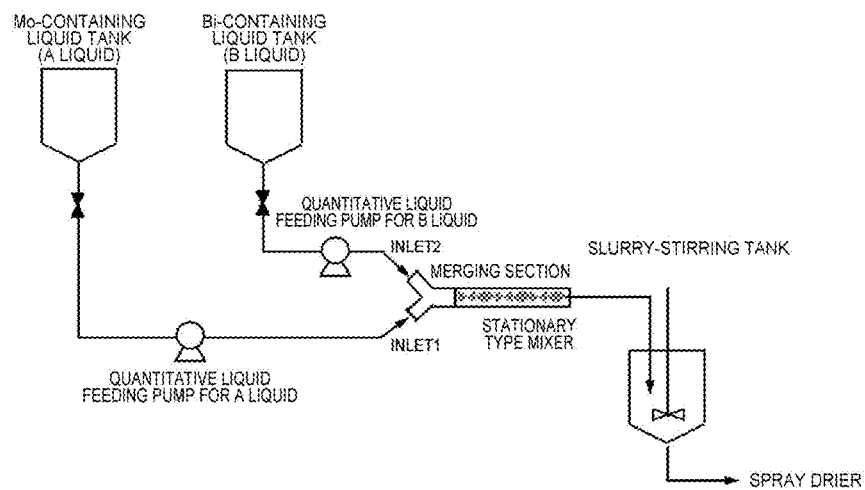
FIG. 1 shows a conceptual diagram illustrating one example of an apparatus for producing a catalyst according to the present embodiment.

Hereinafter, an embodiment for carrying out the present invention (hereinafter, simply referred to as "present embodiment") will be described, but the present invention is not limited to the following embodiment and can be modified variously within the scope thereof.

[Method for Producing Catalyst]

A method for producing a catalyst according to the present embodiment comprises: a preparation step of preparing a precursor slurry comprising molybdenum, bismuth, iron, silica, and a carboxylic acid; a drying step of spray-drying the precursor slurry and thereby obtaining a dried particle; and a calcination step of calcining the dried particle, wherein the preparation step comprises: a step of mixing a starting material for silica with the carboxylic acid and thereby preparing a silica-carboxylic acid mixed liquid; and a step of mixing the silica-carboxylic acid mixed liquid, molybdenum, bismuth, and iron.

By allowing the method for producing a catalyst according to the present embodiment to have the above-described constitution, a catalyst exhibiting a high acrylonitrile yield (and acrylonitrile selectivity) can be obtained. It is to be noted that "high acrylonitrile yield" as referred to herein means that the yield of a resultant acrylonitrile is high when comparison is made among cases where an oxide catalyst whose composition represented by formula (1), which will be described later, is at least the same or approximately the same is used. The present inventors consider this as follows. The active site in the ammoxidation reaction is a bismuth-containing molybdate, but the high acrylonitrile selectivity cannot be obtained with the bismuth-containing molybdate alone. It is considered that complexation of the bismuth-containing molybdate with an iron-containing molybdate and a molybdate that contains another metal improves the acrylonitrile selectivity. Addition of the carboxylic acid to the precursor slurry improves the dispersibility of a bismuth-containing metal component. It is considered that a state in which the bismuth-containing molybdate easily undergoes complexation with a molybdate that contains another metal is created by the addition to improve the acrylonitrile selectivity. In addition, silica is mainly used as a carrier for an ammoxidation catalyst. It is considered that a silanol group existing in silica bonds to a metal component in the slurry to grow into an active site where propylene and acrylonitrile are decomposed, thereby lowering the acrylonitrile selectivity. That is, it is considered that in the step of preparing the precursor slurry, creating a state in which the silanol group and the metal component hardly bond to each other before mixing the metal component and silica contributes to improvements in the acrylonitrile selectivity. However, the mechanism of action is not limited to those described above.

(Composition of Resultant Catalyst)

The catalyst obtained by the production method according to the present embodiment comprises molybdenum, bismuth, and iron as essential components. Molybdenum has a role as a site of adsorbing propylene and a site of activating ammonia. In addition, bismuth has a role of activating propylene and abstracting α hydrogen to produce a π allyl species. Further, iron has a role of supplying oxygen existing in a gas phase to a catalytically active site through trivalent/divalent redox.

Besides, an optional component which may be contained in the catalyst obtained by the production method according to the present embodiment is not particularly limited, and examples thereof include at least one element X selected from the group consisting of nickel, cobalt, magnesium, calcium, zinc, strontium, and barium, at least one element Y selected from the group consisting of cerium, chromium, lanthanum, neodymium, yttrium, praseodymium, samarium, aluminum, gallium, and indium, and at least one element Z selected from the group consisting of potassium, rubidium, and cesium.

The element X in the catalyst obtained by the production method according to the present embodiment forms a molybdate having a moderate amount of lattice defects and has a role of making the transfer of oxygen in a bulk smooth. In addition, the element Y as well as iron has a redox function in the catalyst. Further, the element Z has a role of suppressing decomposition reaction of the main product and of the starting materials by blocking acid centers existing on the surface of the catalyst.

That is, the catalyst obtained by the method for producing a catalyst according to the present embodiment preferably has a composition represented by the following formula (1). By allowing the catalyst to have such a composition, there is a tendency that the acrylonitrile selectivity is further improved.

$$Mo_{12}Bi_aFe_bX_cY_dZ_eO_f \quad (1)$$

In the formula (1), X represents at least one element selected from the group consisting of nickel, cobalt, magnesium, calcium, zinc, strontium, and barium; Y represents at least one element selected from the group consisting of cerium, chromium, lanthanum, neodymium, yttrium, praseodymium, samarium, aluminum, gallium, and indium; and Z represents at least one element selected from the group consisting of potassium, rubidium, and cesium.

In the formula (1), a represents an atomic ratio of bismuth to 12 atoms of molybdenum, and satisfies $0.1 \leq a \leq 3.0$, preferably $0.15 \leq a \leq 1.0$, and more preferably $0.2 \leq a \leq 0.7$.

In the formula (1), b represents an atomic ratio of iron to 12 atoms of molybdenum, and satisfies $0.1 \leq b \leq 3.0$, preferably $0.5 \leq b \leq 2.5$, and more preferably $1.0 \leq b \leq 2.0$.

In the formula (1), c represents an atomic ratio of the element X to 12 atoms of molybdenum, and satisfies $0.1 \leq c \leq 10.0$, preferably $3.0 \leq c \leq 9.0$, and more preferably $5.0 \leq c \leq 8.5$.

In the formula (1), d represents an atomic ratio of the element Y to 12 atoms of molybdenum, and satisfies $0.1 \leq c \leq 13.0$, preferably $0.2 \leq c \leq 12.0$, and more preferably $0.3 \leq d \leq 1.5$.

In the formula (1), e represents an atomic ratio of the element Z to 12 atoms of molybdenum, and satisfies $0.01 \leq e \leq 2.0$, preferably $0.05 \leq e \leq 1.0$.

In the formula (1), f represents an atomic ratio of oxygen to 12 atoms of molybdenum and a value satisfying the balance of atomic valences. It is to be noted that f represents a value corresponding to the number of oxygen atoms needed to satisfy atomic valence requirements of the other existing elements.

Further, in the present embodiment, when the atomic ratio of nickel is denoted as g, and the atomic ratio of cobalt is denoted as h in the formula (1), g and h are preferably adjusted as follows. That is, in a case where the metal oxide does not contain magnesium, $g<1.0$ or $6.5<g$, and $h<1.0$ or $6.5<h$ are preferable. In addition, in a case where the metal oxide contains magnesium, $g<0.5$ or $6.5<g$, and $h<0.5$ or $7.0<h$ are preferable.

In the present embodiment, by appropriately adjusting, for example, starting materials to be used and the amount of use thereof, a resultant catalyst composition can be adjusted in the above-described range.

In addition, the catalyst obtained by the production method according to the present embodiment preferably has a more uniform surface composition of a particle, and specifically, the standard deviation of the values obtained by dividing the ratio of the molar concentration of Bi to the molar concentration of Mo on the surface of the catalyst particle by the ratio of the molar concentration of Bi to the molar concentration of Mo in the metal oxide bulk is preferably 0.2 or less.

The standard deviation will be described later.

In a case where acrylonitrile is industrially produced, a fluidized bed reaction in which a catalyst is fluidized by a reaction gas is generally selected. Therefore, the catalyst preferably has a predetermined or higher strength. From such a viewpoint, the catalyst is carried by a silica carrier. By allowing the catalyst to contain silica as a carrier, lowering of the acrylonitrile selectivity can be suppressed, and the attrition resistance and the particle strength of the catalyst can be greatly improved. The carrier component of the catalyst, other than silica, is not particularly limited, and, for example, an oxide such as alumina, titania, or zirconia can be contained.

The content of the carrier is preferably 30 to 70% by mass, more preferably 35 to 65% by mass, based on the total mass of the catalyst and the carrier. By allowing the content of the carrier to be 30% by mass or more, there is a tendency that the attrition resistance and the particle strength of the catalyst are further improved. By allowing the content of the carrier to be 70% by mass or less, there is a tendency that the acrylonitrile selectivity is further improved.

The starting material for silica to be used as a carrier is not particularly limited, but silica sol is preferable. The primary particle diameter of silica contained in silica sol is not particularly limited, and different types of silica each having a different primary particle diameter may be mixed and used.

(Step (I))

The preparation step in the production method according to the present embodiment comprises a step of mixing a starting material for silica with the carboxylic acid, thereby preparing a silica-carboxylic acid mixed liquid (in the present specification, also referred to as "step (I)"). The order of mixing is not particularly limited, and, for example, the mixed liquid can be obtained by putting a carboxylic acid into a starting material for silica.

As the starting material for silica, silica sol is preferable. The preferable concentration of silica sol in a state of a starting material in which other components are not mixed is 10 to 50% by mass.

The carboxylic acid to be mixed with the starting material for silica is not particularly limited, and examples thereof include oxalic acid, tartaric acid, succinic acid, malic acid, and citric acid. Oxalic acid and tartaric acid are preferable, more preferably oxalic acid. By mixing silica and a carboxylic acid, the silanol group of silica is protected, so that bonding of the silanol group and metal components can be suppressed. In addition, the carboxylic acid is a representative coordinating organic compound, and it is considered that the carboxylic acid facilitates enhancement of dispersibility of metal components by bonding to the metal components. The purity of the carboxylic acid to be used is preferably 99.0% or more. In addition, the carboxylic acid can be added as a solid, such as a powder, or as an aqueous solution.

The content of the carboxylic acid is 0.01 to 0.10 mol equivalents in the precursor slurry, which will be described later, based on the sum of the metal elements constituting the catalyst. The content of the carboxylic acid is more preferably 0.02 to 0.09 mol equivalents, still more preferably 0.02 to 0.07 mol equivalents. By allowing the content of the carboxylic acid to be 0.01 mol equivalents or more, there is a tendency that the acrylonitrile yield of a resultant catalyst is further improved. In addition, by allowing the content of the carboxylic acid to be 0.10 mol equivalents or less, there is a tendency that heat generation due to decomposition or diffusion of the carboxylic acid, or cracking of the catalyst particle is suppressed at a stage of producing the catalyst and the strength of a resultant catalyst is further improved. The content of the carboxylic acid can be adjusted in the above-described ranges according to the ratio of the starting materials added.

The step of putting a carboxylic acid into a starting material for silica is preferably completed quickly. A pH region in which the starting material for silica becomes unstable in water exists, and therefore when the pH region can be passed through in a short time, there is a tendency that the stability of the starting material for silica is improved. The rate of addition of the carboxylic acid is preferably 5 g/sec. per kg of $SiO_2$, more preferably 10 g/sec. per kg of $SiO_2$. By making the rate of addition 5 g/sec. or more, there is a tendency that the aggregation of silica is suppressed to improve the acrylonitrile selectivity and the attrition strength of a resultant catalyst. It is to be noted that "per kg of $SiO_2$" as referred to herein means "per kg of $SiO_2$ contained in the starting material for silica in terms of a solid content".

The stirring time of the silica-carboxylic acid mixed liquid is preferably 60 minutes or less, more preferably 20 minutes or less. By making the stirring time 60 minutes or less, there is a tendency that the aggregation of silica is suppressed to improve the acrylonitrile selectivity and the attrition strength of a resultant catalyst. In addition, the power of stirring the silica-carboxylic acid mixed liquid is preferably 0.01 kW/m$^3$ or more, more preferably 0.03 kW/m$^3$ or more from the viewpoint of mixing silica and the carboxylic acid sufficiently and suppressing particle deposition.

The temperature of stirring the silica-carboxylic acid mixed liquid is preferably 30° C. or more, more preferably 35° C. or more from the viewpoint of improving the dispersibility of the particle.

The pH of the silica-carboxylic acid mixed liquid is preferably 6.50 or less, more preferably 3.00 or less from the viewpoint of improving the dispersibility of silica sol. In a case where the pH of the silica-carboxylic acid mixed liquid is larger than 6.50, there is a tendency that excessive aggregation of silica sol progresses to bring about lowering of the acrylonitrile selectivity and the attrition strength.

(Step (II))

The preparation step in the production method according to the present embodiment comprises a step of mixing the silica-carboxylic acid mixed liquid, molybdenum, bismuth, and iron, thereby obtaining a precursor slurry (in the present specification, also referred to as "step (II)"). The order of mixing is not particularly limited, and, for example, the precursor slurry can be obtained by putting a molybdenum-containing solution into the silica-carboxylic acid mixed liquid, and thereafter putting a solution containing bismuth and iron into a resultant mixture.

The starting material for each component to be used for preparing the starting material slurry is preferably a salt that is soluble to water or nitric acid. It is to be noted that, in the present specification, a slurry that is used for preparing a precursor slurry in the preparation step in the production method according to the present embodiment, the slurry not containing a carboxylic acid, is also referred to as a "starting material slurry". That is, the starting material slurry in the production method according to the present embodiment comprises at least one element selected from the group consisting of molybdenum, bismuth, and iron. The starting material for each element of molybdenum, bismuth, and iron is not particularly limited, and examples thereof include ammonium salts, nitrates, hydrochlorides, sulfates, organic acid salts, and inorganic salts which are soluble to water or nitric acid. Particularly, ammonium salts are preferable as the starting material for molybdenum. In addition, as the starting materials for bismuth and iron, the nitrates of the respective elements are preferable. Nitrates are also preferable in that they are easy to handle, and besides, they do not produce residue of chlorine that is produced in a case where hydrochloric acid is used, or residue of sulfur that is produced in a case where sulfuric acid is used. Examples of the starting material for each component include, but not limited to, ammonium paramolybdate, bismuth nitrate, and ferric nitrate.

(Drying Step)

The drying step is a step of spray-drying the precursor slurry obtained in the preparation step, thereby obtaining a dried particle. By spray-drying the precursor slurry, a spherical, fine particle suitable for fluidized bed reaction can be obtained. A spray-drying apparatus is not particularly limited, and a general apparatus such as a rotary disk type or nozzle type apparatus can be used. By adjusting spray-drying conditions, the particle diameter of the catalyst can be adjusted. In a case where the catalyst is used as a fluidized bed catalyst, the particle diameter of the catalyst is preferably 25 to 180 μm. An example of the condition for obtaining a catalyst particle having a preferable particle diameter includes spray-drying performed using a centrifugal nebulization apparatus provided with a dish type rotor installed at the center of the upper portion of a drier, and holding the temperature of air at the inlet of the drier at 180 to 250° C. and the temperature at the outlet at 100 to 150° C.

In the present embodiment, it is preferable that the step (II) comprise the following (i) step and (ii) step, and the drying step comprise the following (iii) step.

(i) a step of preparing a Mo-containing liquid comprising at least Mo and a Bi-containing liquid comprising at least Bi, (ii) a step of continuously supplying the Mo-containing liquid to a first flow channel, continuously supplying the Bi-containing liquid to a second flow channel, and merging the first flow channel and the second flow channel at downstream from both points of supply of the Mo-containing liquid and the Bi-containing liquid, and consequently mixing the Mo-containing liquid and the Bi-containing liquid to thereby obtain a MoBi-containing liquid, and (iii) a step of drying the MoBi-containing liquid.

In the present embodiment, at least one of the Mo-containing liquid and the Bi-containing liquid can contain the silica-carboxylic acid mixed liquid. In a case where neither the Mo-containing liquid nor the Bi-containing liquid contains the silica-carboxylic acid mixed liquid, that is, in a case where the silica-carboxylic acid mixed liquid is prepared independently of the Mo-containing liquid and the Bi-containing liquid, a step of mixing the silica-carboxylic acid mixed liquid with the Mo-containing liquid and the Bi-containing liquid, or with the MoBi-containing liquid can be carried out.

Further, in the present embodiment, a step of further mixing the MoBi-containing liquid ((iv) step) can be provided after the MoBi-containing liquid (slurry) is produced by mixing the Mo-containing liquid and the Bi-containing liquid and before the step of drying the MoBi-containing liquid (namely between (ii) step and (iii) step).

In addition, a step of storing a certain amount of the MoBi-containing liquid ((v) step) can be provided between the (ii) step and the (iii) step.

The MoBi-containing liquid prepared in the (ii) step may be continuously supplied as prepared to the (iii) step, may be supplied to the (iii) step via the (iv) step, or may be supplied to the (iii) step after part or the whole amount thereof is temporarily stored ((v) step).

In a case where the (v) step is provided to store the MoBi-containing liquid temporarily, the whole amount of the Mo-and-Bi liquid prepared in the (ii) step, or the whole amount of the MoBi-containing liquid prepared by carrying out the (iv) step after the (ii) step is favorably stored (batch treatment methodology). In the case of the batch treatment methodology, even if a deviation in the supply ratio of the Mo-containing liquid to the Bi-containing liquid occurs in the (ii) step, the whole amount of the starting materials is mixed in the (v) step, so that namely the MoBi-containing liquid that is made uniform into an intended composition can be fed to the (iii) step.

In the present embodiment, whether to select the continuous treatment methodology or the batch treatment methodology does not really matter, but it is preferable to select the continuous treatment methodology in a case where a catalyst needs to be produced in a short time and to select the batch treatment methodology in a case where the allowable range of the deviation in the supply ratio is increased.

The (i) step and the (ii) step are steps of preparing a slurry comprising a starting material for a metal oxide.

Specifically, (i) a step of providing a Mo-containing liquid comprising at least Mo (a liquid containing a starting material for Mo to be a component of the metal oxide, hereinafter also referred to as "A liquid") and a Bi-containing liquid comprising at least Bi (a liquid containing a starting material for Bi to be a component of the metal oxide, hereinafter also referred to as "B liquid") and (ii) a step of mixing the two are included (hereinafter, the Mo-containing liquid and the Bi-containing liquid are sometimes referred to as "two liquids"). By mixing the two liquids, the MoBi-containing liquid which is a slurry is formed.

This MoBi-containing liquid is a precursor of a MoBi-containing metal oxide, and it has been found out by an investigation conducted by the present inventors that conditions for producing this precursor have a great influence on the uniformity of the surface composition of a catalyst particle to be produced.

In the (ii) step, by continuously supplying the Mo-containing liquid and the Bi-containing liquid to the first and the second flow channels, respectively, and merging the first flow channel and the second channel at downstream from both points of supply of the Mo-containing liquid and the Bi-containing liquid, thereby preparing a MoBi-containing liquid, there is a tendency that a catalyst particle in which the uniformity of the surface composition is higher is obtained.

It is to be noted that the atomic ratio of respective elements in the metal oxide contained in the catalyst finally produced by this method (bulk composition) are not basically changed from the atomic ratio of starting materials used at the time of production, excluding the oxygen atom.

The starting materials for the elements constituting the catalyst according to the present embodiment are described herein.

The starting material for Mo is preferably a salt that is soluble to water, nitric acid, or the like, and examples thereof include ammonium molybdate which is an ammonium salt.

The starting materials for nickel, cobalt, magnesium, calcium, zinc, strontium, barium, cerium, chromium, lanthanum, neodymium, yttrium, praseodymium, samarium, aluminum, gallium, indium, potassium, rubidium, and cesium are the same as described above and each preferably a salt that is soluble to water, nitric acid, or the like, and examples thereof include nitrates, hydrochlorides, sulfates, and organic acid salts. Particularly, nitrates are preferable from the viewpoint of being easily soluble to water, nitric acid, or the like. Examples thereof include bismuth nitrate, iron nitrate, nickel nitrate, cobalt nitrate, potassium nitrate, rubidium nitrate, magnesium nitrate, calcium nitrate, strontium nitrate, barium nitrate, zinc nitrate, lanthanum nitrate, cerium nitrate, chromium nitrate, indium nitrate, and gallium nitrate. These may be used singly, or two or more of these may be used together.

In addition, the carrier is not particularly limited, and oxides such as silica ($SiO_2$), alumina, titania, and zirconia are preferable. Among these, $SiO_2$ is particularly preferable because lowering of the acrylonitrile selectivity is small, and the number of acid centers that increases by-products is small during reaction for producing acrylonitrile, and the attrition resistance and the particle strength of the catalyst are greatly improved. The starting material for $SiO_2$ is not particularly limited, and examples thereof include silica sol (also referred to as colloidal silica) and powdery silica. Silica sol is particularly preferable because of easiness of handling. Examples thereof include SNOWTEX (manufactured by Nissan Chemical Industries, Ltd.) and Nalco silica sol (manufactured by Nalco Japan Company, Ltd.).

The average primary particle diameter of silica contained in silica sol is not particularly limited, but is preferably in the range of 5 to 100 nm, more preferably in the range of 10 to 50 nm. In addition, different types of silica sol each having a different average primary particle diameter can be mixed and used.

Addition of an inorganic acid such as nitric acid, hydrochloric acid, or sulfuric acid to the Mo-containing liquid, the Bi-containing liquid, and the MoBi-containing liquid in addition to the above-described starting material metals is also preferable. Nitric acid is particularly preferable because it volatilizes during the calcination step, which will be described later, to make a residual in the catalyst small in amount.

Further, addition of ammonia water to the Mo-containing liquid for the purpose of enhancing the solubility of Mo is also preferable.

In the present embodiment, the Mo-containing liquid is preferably prepared by dissolving or dispersing the starting material for Mo in an aqueous medium such as water. Addition of ammonia water to this liquid to enhance the solubility of the starting material for Mo is also preferable. The concentration of the Mo atom in the Mo-containing liquid is preferably within the range of 0.1 to 30% by mass.

In addition, the Bi-containing liquid is preferably prepared separately from the Mo-containing liquid by dissolving or dispersing the starting material for Bi in an aqueous medium such as water. The Bi-containing liquid is preferably acidic, and the Bi-containing liquid more preferably contains nitric acid because nitric acid enhances the solubility of the starting material for Bi. The concentration of the Bi atom in the Bi-containing liquid is preferably within the range of 0.1 to 10% by mass.

The starting materials other than the starting material for Mo and the starting material for Bi, namely the starting materials for Fe, Ni, Co, an alkali metal, Mg, Ca, Sr, Ba, Zn, Mn, rare earth, Cr, In, Ga, Si, Al, Ti, Zr, and the like may be added to any one or both of the Mo-containing liquid and the Bi-containing liquid. Alternatively, these may be added to the MoBi-containing liquid after mixing the two liquids. From the reason that a precipitate is hard to produce, the starting materials for metals other than Mo are preferably added to the Bi-containing liquid, and particularly, the starting materials for metals other than Si, Al, Ti, and Zr are preferably added to the Bi-containing liquid.

In performing the (ii) step, the Mo-containing liquid and the Bi-containing liquid are mixed by continuously supplying the Mo-containing liquid and the Bi-containing liquid to the first and the second flow channels, respectively, and merging the first flow channel and the second flow channel at downstream from both points of supply of the Mo-containing liquid and the Bi-containing liquid.

Supply of the Mo-containing liquid and the Bi-containing liquid to respective flow channels is preferably performed such that the supply molar ratio between Mo and Bi approximately coincides with the ratio of the number of atoms between Mo and Bi in formula (1) which represents a bulk composition of the metal oxide to be produced, namely a/12, and, for example, the supply molar ratio is preferably in the range of $(a/12) \times 0.8$ to $(a/12) \times 1.2$.

That is, in the (ii) step, when the molar supply rates of the Mo-containing liquid and the Bi-containing liquid (however, molar supply rate of Mo and molar supply rate of Bi, respectively) to the first flow channel and the second flow channel, respectively, are denoted as $m\alpha$ (mol/min) and $m\beta$ (mol/min) respectively, the Mo-containing liquid and the Bi-containing liquid are preferably supplied so as to satisfy the following formula (3).

$$(m\beta/m\alpha)/(a/12) = 0.8 \text{ to } 1.2 \qquad (3)$$

It is to be noted that in a case where a batch treatment methodology is adopted in which the (i) step and the (ii) step are each performed batch-wise, and the whole amount of one batch of the MoBi-containing liquid obtained in the (ii) step is fed to the (iii) step after being stored in the (v) step or after being stored in the (v) step via the (iv) step, the Mo-containing liquid and the Bi-containing liquid are preferably supplied such that the ratio of the mass supply rate of the Bi-containing liquid, mB (g/min), to the mass supply rate of the Mo-containing liquid to the first flow channel, mA (g/min), (hereinafter, also referred to as "supply ratio") is 0.5 times to 1.5 times the ratio of the whole amount of the Bi-containing liquid supplied per batch, MB (g), to the whole amount of the Mo-containing liquid supplied per batch, MA (g), (hereinafter, also referred to as "mass ratio").

That is, the Mo-containing liquid and the Bi-containing liquid are preferably supplied so as to satisfy the following formula (2).

$$(mB/mA)/(MB/MA) = 0.5 \text{ to } 1.5 \qquad (2)$$

When the supply ratio is in the range of 0.5 times to 1.5 times the mass ratio, the uniformity of the composition on the surface of the particle of the catalyst can be further enhanced. The (mB/mA)/(MB/MA) is more preferably 0.8 to 1.2, particularly preferably 1.0.

Hereinafter, the supply ratio (mB/mA) and the mass ratio (MB/MA) will be described giving specific examples.

A bulk composition of the metal oxide to be produced is assumed to have a=1 (one atom of Bi to 12 atoms of Mo) in formula (1); one batch of the Mo-containing liquid to be prepared in the (i) step is assumed to contain a needed amount of the starting material for Mo, and the whole amount of the one batch (MA) is assumed to be 100 parts by mass; and one batch of the Bi-containing liquid to be prepared in the (i) step is assumed to contain a needed amount of the starting material for Bi (1/12 of the number of moles of Mo in Mo-containing liquid), and the whole amount of the one batch (MB) is assumed to be 50 parts by mass.

When these two liquids are supplied according to Mo-containing liquid:Bi-containing liquid=100:50 expressed in terms of a ratio between mass amounts supplied per unit time (mass supply rates) (g/min), the mass ratio and the supply ratio are as follows.

Mass ratio (MB/MA)
=50/100=0.5
Supply ratio (mB/mA)
=50/100=0.5

Accordingly, the case corresponds to the supply ratio being 1.0 times the mass ratio.

Similarly, a case where the Mo-containing liquid and the Bi-containing liquid are supplied according to Mo-containing liquid:Bi-containing liquid=100:25 (ratio between mass supply rates) corresponds to the supply ratio being 0.5 times the mass ratio (0.5). A case where the Mo-containing liquid and the Bi-containing liquid are supplied according to Mo-containing liquid:Bi-containing liquid=100:75 (ratio between mass supply rates), (supply ratio=75/100=0.75), corresponds to the supply ratio being 1.5 times the mass ratio (0.5).

In a case where the supply ratio is 1.0 times the mass ratio, which is a particularly preferred embodiment, the two liquids are supplied and merged in the (ii) step at the same ratio as the ratio of the whole amount of one batch of the Bi-containing liquid supplied to the whole amount of one batch of the Mo-containing liquid supplied, and it namely means that the supply molar ratio between Mo and Bi coincides with the molar ratio between Mo and Bi in the bulk composition formula (1) of the metal oxide to be produced, namely coincides with a/12.

In preparation of a slurry in conventional methods for producing a metal oxide catalyst, mixing of a Mo-containing liquid and a Bi-containing liquid is performed by adding any one of the liquids to the other liquid. However, in this method, the concentration of a component which existed in the liquid which is added to the other liquid is small immediately after the mixing starts and is gradually increased as the mixing progresses. In this way, an intended atomic ratio is achieved at the time when addition of the two liquids are completely finished, but a remarkable imbalance is liable to occur between the concentration of a component which existed in the liquid to which the other liquid is added and the concentration of a component which existed in the liquid which is added to the other liquid at a stage in the middle of addition. According to an investigation conducted by the present inventors, it has been found out that this imbalance between the concentration of Bi and of Mo in the mixed liquid during preparation of a slurry is one of the causes which deteriorate the uniformity of the surface composition of a catalyst produced later from the slurry thus prepared.

In contrast, in a case where the two liquids are simultaneously supplied at a merging section in the production method according to the present embodiment, the imbalance, as described above, between the concentrations of the components in the mixed liquid can be made sufficiently small.

Particularly, in a case where the Mo-containing liquid and the Bi-containing liquid are supplied within the range of a particular ratio, a slurry is formed, at any stage of the step of mixing the two, in a state in which the atomic ratio between Mo and Bi in the mixed liquid is close to the atomic ratio in the composition of the catalyst to be produced. By preparing a slurry in such a state, the composition ratio between Mo and Bi on the surface of the finally produced catalyst particle can be made further uniform.

In the present embodiment, in the case where the batch treatment methodology is adopted in which the (i) step and the (ii) step are each performed batch-wise, and the whole amount of one batch of the MoBi-containing liquid obtained in the (ii) step is fed to the (iii) step after being stored in the (v) step or after being stored in the (v) step via the (iv) step, the supply ratio (mB/mA) is, as described above, preferably 0.5 times to 1.5 times the mass ratio (MB/MA). However, the two liquids in the whole amounts are not necessarily contacted with each other in the range of 0.5 times to 1.5 times, and supply of part of the Mo-containing liquid and the Bi-containing liquid may be out of the above-described range.

Specifically, 60% by mass or more of the total amount of the whole amounts of the Mo-containing liquid and the Bi-containing liquid supplied per batch is preferably supplied such that the supply ratio is 0.5 times to 1.5 times the mass ratio, more preferably 80% by mass or more thereof is supplied such that the supply ratio is 0.5 times to 1.5 times the mass ratio, and particularly preferably 100% by mass thereof (namely, in all of the steps in the (ii) step) is supplied such that the supply ratio is 0.5 times to 1.5 times the mass ratio.

This is described by the above-described example of 100 parts by mass of the Mo-containing liquid containing the starting material corresponding to 12 atoms of Mo and 50 parts by mass of the Bi-containing liquid containing the starting material corresponding to 11 atoms of Bi. In this case, the total amount of the whole amounts of the Mo-containing liquid and the Bi-containing liquid supplied is 150 parts by mass, and 60 parts by mass or more thereof corresponds to 90 parts by mass or more.

That is, "supplying 60 parts by mass or more of the total amount of the whole amounts of the two liquids supplied such that the supply ratio is 0.5 times to 1.5 times the mass ratio" corresponds to contacting 90 parts by mass or more of the total amount of the two liquids within the range of Mo-containing liquid:Bi-containing liquid=100:25 to 100:75 in terms of a ratio of the amount supplied per unit time (mass supply rate).

In the (ii) step, the merging temperature when the two liquids are merged is preferably 5° C. to 98° C. The merging temperature is more preferably 35° C. to 98° C., still more preferably 35° C. to 80° C., and particularly preferably 35° C. to 60° C. When merging is performed at 35° C. to 60° C., a catalyst particle having a further uniform surface composition can be produced. The merging temperature herein refers to the liquid temperature of a part where the two liquid are merging and can be measured with a thermometer.

In a case where a step of further mixing the MoBi-containing liquid ((iv) step) is provided in the (ii) step after producing the MoBi-containing liquid (slurry) by mixing the Mo-containing liquid and the Bi-containing liquid and before drying the MoBi-containing liquid, the method of further mixing the produced MoBi-containing liquid is not particularly limited, and examples thereof include allowing the MoBi-containing liquid to pass through a stationary type mixer and stirring the MoBi-containing liquid using a stirrer.

The stirring temperature is preferably set to about the same temperature as the merging temperature in merging the two liquids, and specifically, a merging temperature of 35 to 80° C. is preferable.

In the present embodiment, the configuration of an apparatus for use in the production of a catalyst is not particularly limited, but, for example, an apparatus having a first flow channel for feeding the Mo-containing liquid, a second flow channel for feeding the Bi-containing liquid, and a merging section where the first flow channel and the second flow channel merge is preferable.

The means for supplying the Mo-containing liquid and the Bi-containing liquid to the first and the second flow channels is not particularly limited, but, for example, a quantitative supply apparatus is preferably used. By using a quantitative supply apparatus, the two liquids can be supplied at a further correct ratio. The quantitative supply apparatus is not particularly limited, but a quantitative liquid feeding pump is preferable.

The merging section where the two liquids merge is not particularly limited as long as the two liquids can be merged, and, for example, a pipe having a Y-shape, a T-shape, or the like may be used. The cross-sectional shape of the pipe may be, for example, circular (cylinder), and a mechanism or insert that facilitates mixing of the MoBi-containing liquid is preferably provided inside the pipe. With respect to the angle at which the two liquids are merged, the two liquids may be merged in parallel, perpendicularly, or oppositely.

Providing a mixer for further mixing the MoBi-containing liquid produced at downstream from the merging section is also preferable. One example of the mixer include a stirring tank having a stirrer. FIG. 1 shows one example of such an apparatus configuration. It is to be noted that the above-described respective apparatuses and the like preferably further have an insulating or heating structure, such as a warm-water jacket, which can make the temperature as desired.

Figure 2:
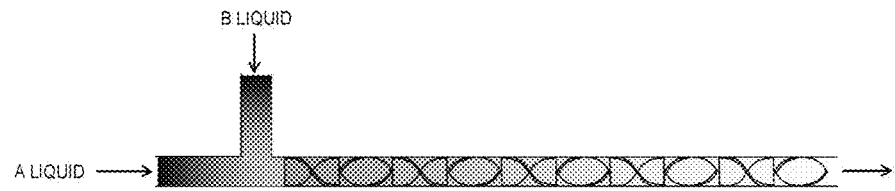
FIG. 2 shows a schematic diagram illustrating one example of a stationary type mixer.

In addition, another example of the mixer include a stationary type mixer (mixer having as main members piping and a twisted plate fixed in the piping, in which fluids supplied in the piping flow along the twisted face to be mixed) as shown in FIG. 2. One example of the stationary type mixer include a static mixer (manufactured by NORITAKE CO., LIMITED). As shown in FIG. 1, a stationary type mixer and a stirring tank may be combined.

By drying the MoBi-containing liquid thus produced ((iii) step), a catalyst comprising a metal oxide having a bulk composition represented by formula (1) can be formed.

The pH of the MoBi-containing liquid is preferably 3 or less before drying. The pH is more preferably 2 or less, still more preferably 1 or less. The pH can be adjusted by, for example, the amount of addition of an acidic solution added to a starting material. When the pH is 3 or less, an increase of the viscosity of the MoBi-containing liquid can be suppressed, so that supply of the MoBi-containing liquid to the (iii) drying step which is the next step can be stably performed.

According to the production method of the present embodiment, the whole slurry preparation step for forming a catalyst precursor can be performed in the form of a liquid, and therefore it can be deemed that the production method of the present embodiment is extremely simpler than methods in which drying, calcination, and pulverization operations, and the like are needed for forming a catalyst precursor.

In the (iii) step, the drying method is not particularly limited, but a dried particle is preferably obtained by spray-drying the above-described MoBi-containing liquid. A spray drier is preferably used for spray-drying in a case, for example, where spray-drying is industrially performed.

In the spray-drying step, the MoBi-containing liquid is first nebulized. This nebulization method is not particularly limited, and examples thereof include a centrifugal system, a two-fluid nozzle system, and a high-pressure nozzle system. Particularly, a centrifugal system is preferable from the viewpoint of not being accompanied by clogging or the like of a nozzle.

The method of drying droplets of the nebulized MoBi-containing liquid is not limited, but, for example, the droplets are preferably dried by hot air in a spray drier. On that occasion, it is preferable that the hot-air inlet temperature be set to 180° C. to 250° C., and the hot-air outlet temperature be set to 100° C. to 150° C.

It is to be noted that a spraying apparatus is preferably adjusted at the time of nebulization such that the sprayed particle diameter falls within a desired range according to the intended particle diameter of a catalyst. For example, in a case where the catalyst is used for fluidized bed reaction, the average particle diameter of the catalyst is preferably about 25 to about 180 μm, and therefore the number of revolutions of a nebulization apparatus (atomizer) is appropriately adjusted such that the average particle diameter falls within this range. In general, the higher the number of revolutions of an atomizer is, the smaller the average particle diameter becomes.

In the present embodiment, by performing: the above-described the MoBi-containing liquid preparation step ((i) step and (ii) step); if necessary, the mixing step ((iv) step) and the storing step ((v) step); and the drying step ((iii) step); and further, the calcination step, which will be described later, as a series of treatments, a catalyst having stable catalytic properties and catalytic performance can be produced quickly and continuously.

In the present embodiment, in a case where both of the (iv) step and the (v) step are performed between the (ii) step and the (iii) step, it is preferable that the (v) step be performed after the (iv) step is performed, or the (iv) step and the (v) step be performed simultaneously (namely, the MoBi-containing liquid be stored while being stirred).

In addition, in a case where a series of treatments of the (i), (ii) and (v) steps or the (i), (ii), (iv), and (v) steps is performed by a batch treatment methodology, the amount of storage in the (v) step is preferably the whole amount of the MoBi-containing liquid obtained in the (ii) step. By supplying the whole amount of the MoBi-containing liquid prepared in the (ii) step after being temporarily stored to the drying step ((iii) step), the ratio of the number of atoms between Mo and Bi in the MoBi-containing liquid to be supplied to the (iii) step can be made equal to the ratio of the number of atoms between the two in formula (1), so that the composition of a resultant catalyst particle can be made nearer to the target even in a case where the amount of the Mo-containing liquid supplied and of the Bi-containing liquid supplied vary in the (ii) step.

The storage container is not limited, and, for example, when a storage container having a stirring function is used, the (v) step and the (iv) step can be performed simultaneously.

Besides those described above, even in a case where, for example, batch mixing of the Mo-containing liquid and the Bi-containing liquid, in which either of the liquids is put into the other liquid using a stirring and mixing tank, is adopted in the preparation of a slurry, the catalyst can also be produced facilitating uniform mixing of the two liquids by making it a rule to produce 50 kg or more of the metal oxide in one batch and making the time required for putting in the liquid which is put into the other liquid within 8 minutes, preferably within 4 minutes. In this case, by making the amount of the Mo/Bi-containing liquid which is put into the other liquid large, there is a tendency that a further uniform mixing of the slurry can be achieved due to a synergistic effect of an increase in collision energy with the liquid into which the other liquid is put by increasing the mass of the liquid which is put into the other liquid; and performing treatment in a short time.

[Calcination Step]

The calcination step is a step of calcining the dried particle obtained in the drying step.

The calcination method is not particularly limited, and examples thereof include static calcination, fluidized calcination, and rotary furnace calcination. Rotary furnace calcination using a rotary kiln is preferable from the viewpoint of capable of performing calcination uniformly.

In a case where the dried particle contains nitric acid, a denitration treatment is preferably performed before the calcination. The denitration treatment is preferably performed at 150 to 450° C. for 1.5 to 3 hours. The calcination can be performed in an air atmosphere.

The calcination temperature in the calcination step is preferably 550 to 650° C. By allowing the calcination temperature to be 550° C. or more, there is a tendency that crystal growth progresses sufficiently and the acrylonitrile selectivity of a resultant catalyst is further improved. In addition, by allowing the calcination temperature to be 650° C. or less, there is a tendency that the specific surface area of a catalyst that can be obtained is increased and the reaction activity of propylene is further improved.

The calcination time is preferably 1 hr to 24 hr, more preferably 2 hr to 20 hr. Conditions such as the calcination temperature and the calcination time are appropriately selected such that desired catalytic properties and reaction performance are obtained.

The catalyst obtained by the production method according to the present embodiment is suitable as a catalyst (ammoxidation catalyst) for use in ammoxidation reaction in the production of acrylonitrile, which will be described later.

[Catalyst]

The catalyst which is obtained by the above-described production method according to the present embodiment is not limited to the catalyst described below, but typically has the following characteristics. That is, the catalyst according to the present embodiment is a catalyst comprising a particle, the particle comprising: a metal oxide having a bulk composition comprising Mo and Bi, the bulk composition represented by the following formula (1); and silica:

$$Mo_{12}Bi_aFe_bX_cY_dZ_eO_f \quad (1)$$

wherein X represents at least one element selected from the group consisting of nickel, cobalt, magnesium, calcium, zinc, strontium, and barium; Y represents at least one element selected from the group consisting of cerium, chromium, lanthanum, neodymium, yttrium, praseodymium, samarium, aluminum, gallium, and indium; Z represents at least one element selected from the group consisting of potassium, rubidium, and cesium; a, b, c, d and e satisfy $0.1 \leq a \leq 2.0$, $0.1 \leq b \leq 3.0$, $0.1 \leq c \leq 10.0$, $0.1 \leq d \leq 3.0$, and $0.01 \leq e \leq 2.0$, and f represents a number of oxygen atoms needed to satisfy atomic valence requirements of the other existing elements.

By containing a metal oxide having the bulk composition, the catalyst according to the present embodiment exhibits a high acrylonitrile selectivity in ammoxidation reaction and has a favorable attrition strength to endure long-term use as a fluidized bed catalyst.

The present inventors consider this as follows. The active site in the ammoxidation reaction is a bismuth-containing molybdate, but the high acrylonitrile selectivity cannot be obtained with the bismuth-containing molybdate alone. It is considered that when uniform complexation of the bismuth-containing molybdate with an iron-containing molybdate and a molybdate that contains another metal is completed at least on the surface of the catalyst particle, the acrylonitrile selectivity is thereby improved.

In addition, it is considered that it is necessary to make the catalyst particle, in which uniform complexation of the bismuth-containing molybdate with the iron-containing molybdate and the molybdate that contains another metal is completed on the surface thereof, at a stage of the precursor slurry thereof, into a state in which the bismuth-containing molybdate easily undergoes complexation with the molybdate that contains another metal by dispersing each metal component as a single component without causing aggregation. Further, in a case where a metal particle is carried on a carrier, it is considered that by preventing the aggregation of both the metals and the carrier particles in the precursor slurry, the attrition strength of the catalyst is improved.

However, the mechanism of action is not limited to those described above.

(Catalyst Composition)

The metal oxide constituting the catalyst in the present embodiment comprises molybdenum, bismuth, and iron as essential components. Molybdenum has a role as a site of adsorbing propylene and a site of activating ammonia. In addition, bismuth has a role of activating propylene and abstracting α hydrogen to produce π allyl species. Further, iron has a role of supplying oxygen existing in a gas phase to catalytically active site through trivalent/divalent redox.

Besides, examples of an optional component which may be contained in the metal oxide include at least one element X selected from the group consisting of nickel, cobalt, magnesium, calcium, zinc, strontium, and barium, at least one element Y selected from the group consisting of cerium, chromium, lanthanum, neodymium, yttrium, praseodymium, samarium, aluminum, gallium, and indium, and at least one element Z selected from the group consisting of potassium, rubidium, and cesium. The element X forms a molybdate having a moderate amount of lattice defects and has a role of making the transfer of oxygen within a bulk smooth. The element Y as well as iron has a redox function in the catalyst. Further, the element Z has a role of suppressing decomposition reaction of the main product and of the starting materials by blocking acid centers existing on the surface of the catalyst.

As described above, each element is equipped with its role for functioning as a catalyst, and there exist an element that can replace the function of such an element, an element that cannot replace the function of such an element, an element that brings about auxiliary action, and the like, and therefore an element which it is better to add and its composition ratio are different depending on the element constitution and the composition of the catalyst.

The bulk composition of the metal oxide constituting the catalyst according to the present embodiment, namely the ratio of respective elements constituting the whole metal oxide is represented by the following formula (1).

By allowing the ammoxidation catalyst to have such a composition, there is a tendency that the acrylonitrile selectivity is further improved.

$$Mo_{12}Bi_aFe_bX_cY_dZ_eO_f \quad (1)$$

In the formula (1), X represents at least one element selected from the group consisting of nickel, cobalt, magnesium, calcium, zinc, strontium, and barium; Y represents at least one element selected from the group consisting of cerium, chromium, lanthanum, neodymium, yttrium, praseodymium, samarium, aluminum, gallium, and indium; and Z represents at least one element selected from the group consisting of potassium, rubidium, and cesium;

a represents an atomic ratio of bismuth to 12 atoms of molybdenum, and satisfies $0.1 \leq a \leq 2.0$, preferably $0.15 \leq a \leq 1.0$, and more preferably $0.2 \leq a \leq 0.7$;

b represents an atomic ratio of iron to 12 atoms of molybdenum, and satisfies $0.1 \leq b \leq 3.0$, preferably $0.5 \leq b \leq 2.5$, and more preferably $1.0 \leq b \leq 2.0$;

c represents an atomic ratio of the X to 12 atoms of molybdenum, and satisfies $0.1 \leq c \leq 10.0$, preferably $3.0 \leq c \leq 9.0$, and more preferably $5.0 \leq c \leq 8.5$;

d represents an atomic ratio of the Y to 12 atoms of molybdenum, and satisfies $0.1 \leq c \leq 13.0$, preferably $0.2 \leq c \leq 12.0$, and more preferably $0.3 \leq c \leq 11.5$;

e represents an atomic ratio of the Z to 12 atoms of molybdenum, and satisfies $0.01 \leq e \leq 2.0$, preferably $0.05 \leq e \leq 1.0$; and f represents an atomic ratio of oxygen to 12 atoms of molybdenum and a number of oxygen atoms needed to satisfy atomic valence requirements of the other existing elements.

Further, in the present embodiment, the atomic ratio of nickel is denoted as g, and the atomic ratio of cobalt is denoted as h in the formula (1), g and h are preferably adjusted as follows. That is, in a case where the metal oxide does not contain magnesium, $g<1.0$ or $6.5<g$, and $h<1.0$ or $6.5<h$ are preferable. In addition, in a case where the metal oxide contains magnesium, $g<0.5$ or $6.5<g$, and $h<0.5$ or $7.0<h$ are preferable.

It is to be noted that the bulk composition (each element ratio) of the metal oxide can be determined by the ratio of the starting materials added at the time of synthesizing the catalyst and well-known methods of quantitative analysis of elements such as ICP atomic emission spectrometry, atomic absorption spectrophotometry, ICP mass spectrometry, and fluorescent X-ray analysis.

The ICP atomic emission spectrometry is a method adopted in Examples, and the specific procedure will be described in Examples. In addition, in a case of quantitative analysis by fluorescent X-ray spectroscopy, the quantitative analysis of a catalyst sample can be performed using, for example, a fluorescent X-ray apparatus (for example, ZSX 100e (tube: Rh-4KW, analyzing crystal: LiF, PET, Ge, RX25) manufactured by Rigaku Corporation) based on a calibration curve for correcting a matrix effect of each element. It is to be noted that in a case where the catalyst is produced by the production method according to the present embodiment, which will be described later, a value obtained by such analysis almost coincides with the designed composition corresponding to the starting materials added. In addition, according to these types of quantitative analysis of elements, the bulk composition of the catalyst before use and of the catalyst in use can be determined.

In a case where acrylonitrile is industrially produced, a fluidized bed reaction in which a catalyst is fluidized by a reaction gas is generally selected. Therefore, in a case where the catalyst according to the present embodiment is used as an ammoxidation catalyst, the catalyst according to the present embodiment preferably has a predetermined or higher strength. From such a viewpoint, the metal oxide is carried by a silica-containing carrier in the catalyst according to the present embodiment. By allowing the catalyst according to the present embodiment to contain silica as a carrier, lowering of the acrylonitrile selectivity can be suppressed, and the attrition resistance and the particle strength of the catalyst can be greatly improved. The carrier component of the catalyst, other than silica, is not particularly limited, and, for example, an oxide such as alumina, titania, or zirconia can be contained.

The content of the carrier is preferably 30 to 70% by mass, more preferably 35 to 65% by mass, based on 100% by mass of the mass of the catalyst. By allowing the content of the carrier to be 30% by mass or more, there is a tendency that the attrition resistance and the particle strength of the ammoxidation catalyst is further improved. By allowing the content of the carrier to be 70% by mass or less, there is a tendency that the acrylonitrile selectivity is further improved.

In the present embodiment, the shape of the catalyst particle is not particularly limited, but the shape is preferably a spherical shape. In addition, the average particle diameter of the catalyst particle is preferably within the range of 40 to 70 µm, more preferably within the range of 45 to 65 µm. As a particle diameter distribution, the amount of the catalyst particle having a particle diameter of 5 to 200 µm is preferably 90 to 100% by mass based on the total mass of the catalyst. In addition, the amount of the particle having a particle diameter of 45 µm or less is preferably 10 to 50% by volume, more preferably in the range of 15 to 35% by volume, based on the total volume of the particle.

In addition, the catalyst according to the present embodiment preferably has an excellent attrition resistance strength such that it can be used as a fluidized bed catalyst. Particularly in the fluidized bed reaction, the catalyst is preferably equipped with attrition resistance strength to such an extent that wear or crush of the catalyst particle does not occur due to shock such as contact between catalyst particles in a reactor, collision with a wall face of a reactor, or contact with a gas, and from such a viewpoint, the catalyst according to the present embodiment preferably has a wear loss of 2.5% or less, the wear loss described in the wear test of a fluidized bed catalyst (test according to the method described in "Test Method for Synthetic Fluid Cracking Catalyst" (American Cyanamid Co. Ltd. 6/31-4m-1/57)).

Further, the apparent specific gravity of the catalyst particle according to the present embodiment is preferably in the range of 0.85 to 1.15 g/cc. In a case where the apparent specific gravity of the catalyst particle is 0.85 g/cc or more, there is a tendency that an influence of the bulkiness of the catalyst particle in putting the catalyst particle into a reactor can be reduced and the volume of the reactor to be required can be reduced, and besides, there is a tendency that occurrence of catalyst loss due to an increase in the amount of the catalyst which scatters outside from the reactor can be effectively prevented. In addition, in a case where the apparent specific gravity of the catalyst particle is 1.15 g/cc or less, there is a tendency that a favorable flowing state of the catalyst particle can be secured and lowering of the reaction performance can be effectively prevented.

It is to be noted that the apparent specific gravity of the catalyst particle can be determined such that a specimen (catalyst particle) is placed under a constant condition in a container having a constant volume, and the mass of the specimen placed in the container is measured to calculate the mass per unit volume.

For example, a 25-ml measuring cylinder of glass (hereinafter, simply referred to as "measuring cylinder") is disposed right under a glass funnel, a measurement specimen (catalyst particle) which has been shaken well in advance is dropped to the glass funnel, and the specimen is put into the measuring cylinder until the specimen overflows from the measuring cylinder. The convex portion of the specimen accumulated over the mouth of the measuring cylinder is leveled off and removed, and the specimen adhering to the outer wall of the measuring cylinder is swept away with a brush or the like. The mass of the specimen is determined from the mass of the measuring cylinder in which the specimen is placed and the mass of the measuring cylinder which has been measured in advance, and the apparent specific gravity is calculated by dividing the mass of the specimen by the volume of the measuring cylinder.

In the present embodiment, a standard deviation of a value obtained by dividing the ratio of the molar concentration of Bi to the molar concentration of Mo on the surface of the catalyst particle, $((Bi/Mo)_{surf})$, by the ratio of the molar concentration of Bi to the molar concentration of Mo in the metal oxide bulk, $((Bi/Mo)_{bulk})$, of the catalyst comprising a metal oxide having a bulk composition represented by formula (1) is 0.2 or less.

The molar concentration of Mo and the molar concentration of Bi on the surface of the particle herein can be determined by SEM-EDX (Scanning Electron Microscopes-Energy Dispersive X-ray Spectroscopy) composition analysis, and the molar concentration of Mo and the molar concentration of Bi in the metal oxide bulk can be determined, as described above, by, for example, the ICP atomic emission spectrometry.

In addition, the standard deviation can be determined by the following formula (4).

$$\text{Standard deviation} = \{((S_1-\mu)^2+(S_2-\mu)^2+\ldots+(S_{100}-\mu)^2)/100[\text{Number}]\}^{1/2} \quad (4)$$

In formula (4), $S_k$ (k=1 to 100) represents a value obtained by dividing the ratio of the measured value of the molar concentration of Bi to the molar concentration of Mo on the surface of the kth particle among 100 arbitrarily selected particles, $(Bi/Mo)_{surf}$, by the ratio of the molar concentration of Bi to the molar concentration of Mo in the metal oxide bulk, $(Bi/Mo)_{bulk}$, and μ represents an average value $(=(S_1+ S_2 \ldots +S_{100})/100)$ of 100 $S_k$s (k=100).

The standard deviation is an index of variation. The smaller the standard deviation is, the smaller the variation from the average value is. Accordingly, a smaller value of formula (4) means a more uniform surface composition of the particle.

According to an investigation conducted by the present inventors, it has been made clear that when a catalyst having a small value of formula (4) is used in producing acrylonitrile through ammoxidation reaction of propylene, the acrylonitrile yield is enhanced. The value of formula (4) is 0.2 or less, preferably 0.15 or less, more preferably 0.10 or less, and still more preferably 0.07 or less in the present embodiment.

[Method for Producing Acrylonitrile]

A method for producing acrylonitrile according to the present embodiment comprises: a step of obtaining a catalyst by the above-described method for producing a catalyst; and a reaction step of reacting propylene, molecular oxygen, and ammonia in the presence of the resultant catalyst, thereby producing acrylonitrile. In addition, the method for producing acrylonitrile according to the present embodiment can also be described as a method for producing acrylonitrile comprising a step of reacting propylene, molecular oxygen, and ammonia in the presence of the catalyst according to the present embodiment.

Production of acrylonitrile through ammoxidation reaction can be performed by a fixed bed reactor or a fluidized bed reactor. Among these, the fluidized bed reactor is preferable from the viewpoint of efficiently removing heat generated during reaction and enhancing the yield of acrylonitrile.

Propylene and ammonia each being a starting material in the ammoxidation reaction are not necessarily of high purity, and propylene and ammonia of industrial grade can be used. The molar ratio of propylene, ammonia, and oxygen (propylene/ammonia/oxygen) in the starting material gas is preferably 1.0/1.0 to 1.5/1.6 to 2.2.

A molecular oxygen-containing gas which is usable in the method for producing acrylonitrile according to the present embodiment is not particularly limited, and examples thereof include air, oxygen-enriched air, and pure oxygen; gases obtained by diluting these with an inert gas, such as helium, argon, carbon dioxide, or nitrogen, or water vapor. Among these, in a case where the gas is used in an industrial scale, air is preferably used because of simplicity.

The reaction temperature is preferably 380 to 480° C. In addition, the reaction pressure is preferably normal pressure to 0.3 MPa. The contact time between the starting material gas and the catalyst is preferably 2 to 7 seconds, more preferably 3 to 6 seconds.

EXAMPLES

Hereinafter, the present embodiment will be described in more detail giving Examples, but the present embodiment is not limited to Examples described below. It is to be noted that catalyst composition described in Examples and Comparative Examples has the same value as the composition of each element added. In Examples and Comparative Examples, values and procedures for obtaining 1 kg of a catalyst after calcination are described.

Example 1

A catalyst in which a metal oxide having a bulk composition (hereinafter, simply referred to as "composition") represented by $Mo_{12.00}Bi_{0.50}Fe_{1.31}Co_{4.05}Ni_{3.10}Ce_{0.87}Rb_{0.10}K_{0.08}O_f$ (compositions after this are described omitting "$O_f$") is carried on 40% by mass of silica was produced according to the following procedure.

To 1333 g of silica sol containing 30% by mass of $SiO_2$ and having pH=9.00, 25.0 g of oxalic acid dihydrate (purity of 99.5%) dissolved in 200 g of water was added (in the precursor slurry, 0.040 mol equivalents based on the sum of the metal elements). The pH was measured with a pH recording meter (DKK-TOA CORPORATION, HM-30P). The rate of addition on that occasion was 12 g/sec. (per kg of $SiO_2$). On that occasion, the pH of the silica-oxalic acid mixed liquid was 1.65. The silica-oxalic acid mixed liquid was mixed at 0.2 kW/m³ and 40° C. for 10 minutes. Subsequently, to the silica-oxalic acid mixed liquid, 481.6 g of ammonium paramolybdate $[(NH_4)_6Mo_7O_{24}.4H_2O]$ dissolved in 865.8 g of water was added under stirring, and further 55.1 g of bismuth nitrate $[Bi(NO_3)_3.5H_2O]$, 120.3 g of iron nitrate $[Fe(NO_3)_3.9H_2O]$, 268.0 g of cobalt nitrate $[Co(NO_3)_2.6H_2O]$, 204.9 g of nickel nitrate $[Ni(NO_3)_2.6H_2O]$, 85.9 g of cerium nitrate $[Ce(NO_3)_3.6H_2O]$, 3.35 g of rubidium nitrate $[RbNO_3]$, and 1.84 g of potassium nitrate $[KNO_3]$ dissolved in 391.8 g of 16.6% by mass of nitric acid were added to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried particle was held at 200° C. for 5 minutes, the temperature was then raised from 200° C. to 450° C. at 2.5° C./min, and the dried particle was then held at 450° C. for 20 minutes to perform denitration. The resultant denitrated powder was calcined at 590° C. for 2 hours to obtain a catalyst.

Example 2

A catalyst was produced in the same manner as in Example 1 except that the time of stirring the silica-oxalic acid mixed liquid was changed to 30 minutes.

Example 3

A catalyst was produced in the same manner as in Example 1 except that the time of stirring the silica-oxalic acid mixed liquid was changed to 80 minutes.

Example 4

A catalyst was produced in the same manner as in Example 1 except that the rate of addition of oxalic acid was changed to 8 g/sec. (per kg of $SiO_2$).

Example 5

A catalyst was produced in the same manner as in Example 1 except that the rate of addition of oxalic acid was changed to 3 g/sec. (per kg of $SiO_2$).

Example 6

A catalyst in which a metal oxide having a composition represented by $Mo_{12.00}Bi_{0.39}Fe_{1.60}Ni_{6.97}Mg_{0.77}Ce_{0.63}Rb_{0.17}$ is carried on 40% by mass of silica was produced according to the following procedure.

To 1333 g of silica sol containing 30% by mass of $SiO_2$ and having pH=9.00, 25.0 g of oxalic acid dihydrate (purity of 99.5%) dissolved in 200 g of water was added (in the precursor slurry, 0.038 mol equivalents based on the sum of the metal elements). The pH was measured with a pH recording meter (DKK-TOA CORPORATION, HM-30P). The rate of addition on that occasion was 12 g/sec. (per kg of $SiO_2$). On that occasion, the pH of the silica-oxalic acid mixed liquid was 1.65. The silica-oxalic acid mixed liquid was mixed at 0.2 $kW/m^3$ and 40° C. for 10 minutes. Subsequently, to the silica-oxalic acid mixed liquid, 485.9 g of ammonium paramolybdate $[(NH_4)_6Mo_7O_{24}.4H_2O]$ dissolved in 873.5 g of water was added under stirring, and further 43.1 g of bismuth nitrate $[Bi(NO_3)_3.5H_2O]$, 148.0 g of iron nitrate $[Fe(NO_3)_3.9H_2O]$, 464.7 g of nickel nitrate $[Ni(NO_3)_2.6H_2O]$, 45.5 g of magnesium nitrate $[Mg(NO_3)_2.6H_2O]$, 62.6 g of cerium nitrate $[Ce(NO_3)_3.6H_2O]$, and 5.89 g of rubidium nitrate $[RbNO_3]$ dissolved in 396.7 g of 16.6% by mass of nitric acid were added to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried particle was held at 200° C. for 5 minutes, the temperature was then raised from 200° C. to 450° C. at 2.5° C./min, and the dried particle was then held at 450° C. for 20 minutes to perform denitration. The resultant denitrated powder was calcined at 580° C. for 2 hours to obtain a catalyst.

Example 7

A catalyst was produced in the same manner as in Example 6 except that the time of stirring the silica-oxalic acid mixed liquid was changed to 80 minutes.

Example 8

A catalyst was produced in the same manner as in Example 6 except that the rate of addition of oxalic acid was changed to 3 g/sec. (per kg of $SiO_2$).

Example 9

A catalyst in which a metal oxide having a composition represented by $Mo_{12.00}Bi_{1.20}Fe_{0.60}Ni_{7.80}Cr_{1.20}K_{0.48}$ is carried on 60% by mass of silica was produced according to the following procedure.

To 2000 g of silica sol containing 30% by mass of $SiO_2$ and having pH=9.00, 25.0 g of oxalic acid dihydrate (purity of 99.5%) dissolved in 200 g of water was added (in the precursor slurry, 0.059 mol equivalents based on the sum of the metal elements). The pH was measured with a pH recording meter (DKK-TOA CORPORATION, HM-30P). The rate of addition on that occasion was 12 g/sec. (per kg of $SiO_2$). On that occasion, the pH of the silica-oxalic acid mixed liquid was 1.76. The silica-oxalic acid mixed liquid was mixed at 0.2 $kW/m^3$ and 40° C. for 10 minutes. Subsequently, to the silica-oxalic acid mixed liquid, 308.0 g of ammonium paramolybdate $[(NH_4)_6Mo_7O_{24}.4H_2O]$ dissolved in 553.7 g of water was added under stirring, and further 84.6 g of bismuth nitrate $[Bi(NO_3)_3.5H_2O]$, 35.2 g of iron nitrate $[Fe(NO_3)_3.9H_2O]$, 329.8 g of nickel nitrate $[Ni(NO_3)_2.6H_2O]$, 69.8 g of chromium nitrate $[Cr(NO_3)_3.9H_2O]$, and 7.06 g of potassium nitrate $[KNO_3]$ dissolved in 387.6 g of 16.6% by mass of nitric acid were added to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried particle was held at 200° C. for 5 minutes, the temperature was then raised from 200° C. to 450° C. at 2.5° C./min, and the dried particle was then held at 450° C. for 20 minutes to perform denitration. The resultant denitrated powder was calcined at 590° C. for 2 hours to obtain a catalyst.

Example 10

A catalyst in which a metal oxide having a composition represented by $Mo_{12.00}Bi_{2.40}Fe_{2.40}Ni_{6.00}Zn_{1.30}Ce_{0.24}K_{0.24}$ is carried on 60% by mass of silica was produced according to the following procedure.

To 2000 g of silica sol containing 30% by mass of $SiO_2$ and having pH=9.00, 25.0 g of oxalic acid dihydrate (purity of 99.5%) dissolved in 200 g of water was added (in the precursor slurry, 0.061 mol equivalents based on the sum of the metal elements). The pH was measured with a pH recording meter (DKK-TOA CORPORATION, HM-30P). The rate of addition on that occasion was 12 g/sec. (per kg of $SiO_2$). On that occasion, the pH of the silica-oxalic acid mixed liquid was 1.76. The silica-oxalic acid mixed liquid was mixed at 0.2 $kW/m^3$ and 40° C. for 10 minutes. Subsequently, to the silica-oxalic acid mixed liquid, 271.3 g of ammonium paramolybdate $[(NH_4)_6Mo_7O_{24}.4H_2O]$ dissolved in 487.7 g of water was added under stirring, and further 149.1 g of bismuth nitrate $[Bi(NO_3)_3.5H_2O]$, 124.2 g of iron nitrate $[Fe(NO_3)_3.9H_2O]$, 223.5 g of nickel nitrate $[Ni(NO_3)_2.6H_2O]$, 68.6 g of zinc nitrate $[Zn(NO_3)_2.6H_2O]$, 13.3 g of cerium nitrate $[Ce(NO_3)_3.6H_2O]$, and 3.11 g of potassium nitrate $[KNO_3]$ dissolved in 382.2 g of 16.6% by mass of nitric acid were added to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried particle was held at 200° C. for 5 minutes, the temperature was then raised from 200° C. to 450° C. at 2.5° C./min, and the dried particle was then held at 450° C. for 20 minutes to perform denitration. The resultant denitrated powder was calcined at 570° C. for 2 hours to obtain a catalyst.

Example 11

A catalyst in which a metal oxide having a composition represented by $Mo_{12.00}Bi_{0.47}Fe_{1.35}Co_{4.15}Ni_{3.00}Ce_{0.91}Rb_{0.14}$ is carried on 40% by mass of silica was produced according to the following procedure.

To 1333 g of silica sol containing 30% by mass of $SiO_2$ and having pH=9.00, 25.0 g of oxalic acid dihydrate (purity of 99.5%) dissolved in 200 g of water was added (in the precursor slurry, 0.040 mol equivalents based on the sum of the metal elements). The pH was measured with a pH recording meter (DKK-TOA CORPORATION, HM-30P). The rate of addition on that occasion was 12 g/sec. On that occasion, the pH of the silica-oxalic acid mixed liquid was 1.65. The silica-oxalic acid mixed liquid was mixed at 0.2 $kW/m^3$ and 40° C. for 10 minutes. Subsequently, to the silica-oxalic acid mixed liquid, 481.1 g of ammonium paramolybdate $[(NH_4)_6Mo_7O_{24}.4H_2O]$ dissolved in 864.9 g of water was added under stirring, and further 51.8 g of bismuth nitrate [Bi(NO$_3$)$_3$.5H$_2$O], 123.9 g of iron nitrate [Fe(NO$_3$)$_3$.9H$_2$O], 274.4 g of cobalt nitrate [Co(NO$_3$)$_2$.6H$_2$O], 198.1 g of nickel nitrate [Ni(NO$_3$)$_2$.6H$_2$O], 89.7 g of cerium nitrate [Ce(NO$_3$)$_3$.6H$_2$O], and 4.81 g of rubidium nitrate [RbNO$_3$] dissolved in 392.0 g of 16.6% by mass of nitric acid were added to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried particle was held at 200° C. for 5 minutes, the temperature was then raised from 200° C. to 450° C. at 2.5° C./min, and the dried particle was then held at 450° C. for 20 minutes to perform denitration. The resultant denitrated powder was calcined at 590° C. for 2 hours to obtain a catalyst.

Example 12

A catalyst in which a metal oxide having a composition represented by Mo$_{12.00}$Bi$_{0.57}$Fe$_{1.01}$Co$_{6.83}$Ni$_{0.98}$Mg$_{0.98}$Ce$_{0.38}$Rb$_{0.12}$ is carried on 40% by mass of silica was produced according to the following procedure.

To 1333 g of silica sol containing 30% by mass of SiO$_2$ and having pH=8.00, 50.0 g of oxalic acid dihydrate (purity of 99.5%) dissolved in 200 g of water was added (in the precursor slurry, 0.076 mol equivalents based on the sum of the metal elements). The pH was measured with a pH recording meter (DKK-TOA CORPORATION, HM-30P). The rate of addition on that occasion was 12 g/sec. On that occasion, the pH of the silica-oxalic acid mixed liquid was 1.10. The silica-oxalic acid mixed liquid was mixed at 0.2 kW/m$^3$ and 40° C. for 10 minutes. Subsequently, to the silica-oxalic acid mixed liquid, 482.0 g of ammonium paramolybdate [(NH$_4$)$_6$Mo$_7$O$_{24}$.4H$_2$O] dissolved in 866.4 g of water was added under stirring, and further 62.7 g of bismuth nitrate [Bi(NO$_3$)$_3$.5H$_2$O], 93.0 g of iron nitrate [Fe(NO$_3$)$_3$.9H$_2$O], 452.3 g of cobalt nitrate [Co(NO$_3$)$_2$.6H$_2$O], 64.5 g of nickel nitrate [Ni(NO$_3$)$_2$.6H$_2$O], 56.9 g of magnesium nitrate [Mg(NO$_3$)$_2$.6H$_2$O], 37.4 g of cerium nitrate [Ce(NO$_3$)$_3$.6H$_2$O], and 3.93 g of rubidium nitrate [RbNO$_3$] dissolved in 395.2 g of 16.6% by mass of nitric acid were added to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 590° C. for 2 hours to obtain a catalyst.

Example 13

A catalyst was produced in the same manner as in Example 12 except that the pH of the silica sol is 9.00, the amount of oxalic acid dihydrate is 25.0 g (in the precursor slurry, 0.038 mol equivalents based on the sum of the metal elements), and the pH of the silica-oxalic acid mixed liquid is 1.65.

Example 14

A catalyst was produced in the same manner as in Example 12 except that the pH of the silica sol is 9.70, the amount of oxalic acid dihydrate is 25.0 g (in the precursor slurry, 0.038 mol equivalents based on the sum of the metal elements), and the pH of the silica-oxalic acid mixed liquid is 5.30.

Example 15

A catalyst was produced in the same manner as in Example 12 except that the pH of the silica sol is 10.13, the amount of oxalic acid dihydrate is 25.0 g (in the precursor slurry, 0.038 mol equivalents based on the sum of the metal elements), and the pH of the silica-oxalic acid mixed liquid is 8.00.

Example 16

A catalyst in which a metal oxide having a composition represented by Mo$_{12.00}$Bi$_{0.57}$Fe$_{1.01}$Co$_{2.24}$Ni$_{6.54}$Ce$_{0.38}$Rb$_{0.12}$ is carried on 40% by mass of silica was produced according to the following procedure.

To 1333 g of silica sol containing 30% by mass of SiO$_2$ and having pH=8.00, 50.0 g of oxalic acid dihydrate (purity of 99.5%) dissolved in 200 g of water was added (in the precursor slurry, 0.077 mol equivalents based on the sum of the metal elements). The pH was measured with a pH recording meter (DKK-TOA CORPORATION, HM-30P). The rate of addition on that occasion was 12 g/sec. On that occasion, the pH of the silica-oxalic acid mixed liquid was 1.10. The silica-oxalic acid mixed liquid was mixed at 0.2 kW/m$^3$ and 40° C. for 10 minutes. Subsequently, to the silica-oxalic acid mixed liquid, 479.5 g of ammonium paramolybdate [(NH$_4$)$_6$Mo$_7$O$_{24}$.4H$_2$O] dissolved in 855.9 g of water was added under stirring, and further 61.9 g of bismuth nitrate [Bi(NO$_3$)$_3$.5H$_2$O], 91.9 g of iron nitrate [Fe(NO$_3$)$_3$.9H$_2$O], 146.8 g of cobalt nitrate [Co(NO$_3$)$_2$.6H$_2$O], 427.2 g of nickel nitrate [Ni(NO$_3$)$_2$.6H$_2$O], 36.9 g of cerium nitrate [Ce(NO$_3$)$_3$.6H$_2$O], and 3.88 g of rubidium nitrate [RbNO$_3$] dissolved in 393.2 g of 16.6% by mass of nitric acid were added to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 600° C. for 2 hours to obtain a catalyst.

Example 17

A catalyst was produced in the same manner as in Example 16 except that the pH of the silica sol is 9.00, the amount of oxalic acid dihydrate is 25.0 g (in the precursor slurry, 0.039 mol equivalents based on the sum of the metal elements), and the pH of the silica-oxalic acid mixed liquid is 1.65.

Example 18

A catalyst was produced in the same manner as in Example 16 except that the pH of the silica sol is 9.70, the amount of oxalic acid dihydrate is 25.0 g (in the precursor slurry, 0.039 mol equivalents based on the sum of the metal elements), and the pH of the silica-oxalic acid mixed liquid is 5.30.

Example 19

A catalyst was produced in the same manner as in Example 16 except that the pH of the silica sol is 10.13, the amount of oxalic acid dihydrate is 25.0 g (in the precursor slurry, 0.039 mol equivalents based on the sum of the metal elements), and the pH of the silica-oxalic acid mixed liquid is 8.00.

Example 20

A catalyst in which a metal oxide having a composition represented by $Mo_{12.00}Bi_{0.84}Fe_{2.06}Co_{6.67}Ce_{0.56}Rb_{0.12}$ is carried on 40% by mass of silica was produced according to the following procedure.

To 1333 g of silica sol containing 30% by mass of $SiO_2$ and having pH=8.00, 50.0 g of oxalic acid dihydrate (purity of 99.5%) dissolved in 200 g of water was added (in the precursor slurry, 0.080 mol equivalents based on the sum of the metal elements). The pH was measured with a pH recording meter (DKK-TOA CORPORATION, HM-30P). The rate of addition on that occasion was 12 g/sec. On that occasion, the pH of the silica-oxalic acid mixed liquid was 1.10. The silica-oxalic acid mixed liquid was mixed at 0.2 kW/m$^3$ and 40° C. for 10 minutes. Subsequently, to the silica-oxalic acid mixed liquid, 472.5 g of ammonium paramolybdate [$(NH_4)_6Mo_7O_{24}.4H_2O$] dissolved in 849.4 g of water was added under stirring, and further 90.7 g of bismuth nitrate [$Bi(NO_3)_3.5H_2O$], 185.4 g of iron nitrate [$Fe(NO_3)_3.9H_2O$], 432.8 g of cobalt nitrate [$Co(NO_3)_2.6H_2O$], 54.4 g of cerium nitrate [$Ce(NO_3)_3.6H_2O$], and 3.96 g of rubidium nitrate [$RbNO_3$] dissolved in 391.6 g of 16.6% by mass of nitric acid were added to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 580° C. for 2 hours to obtain a catalyst.

Example 21

A catalyst was produced in the same manner as in Example 20 except that the pH of the silica sol is 9.00, the amount of oxalic acid dihydrate is 25.0 g (in the precursor slurry, 0.040 mol equivalents based on the sum of the metal elements), and the pH of the silica-oxalic acid mixed liquid is 1.65.

Example 22

A catalyst was produced in the same manner as in Example 20 except that the pH of the silica sol is 9.70, the amount of oxalic acid dihydrate is 25.0 g (in the precursor slurry, 0.040 mol equivalents based on the sum of the metal elements), and the pH of the silica-oxalic acid mixed liquid is 5.30.

Example 23

A catalyst was produced in the same manner as in Example 20 except that the pH of the silica sol is 10.13, the amount of oxalic acid dihydrate is 25.0 g (in the precursor slurry, 0.040 mol equivalents based on the sum of the metal elements), and the pH of the silica-oxalic acid mixed liquid is 8.00.

Example 24

A catalyst in which a metal oxide having a composition represented by $Mo_{12.00}Bi_{0.27}Fe_{0.95}Co_{6.69}Ni_{2.95}Ce_{0.18}Rb_{0.13}$ is carried on 40% by mass of silica was produced according to the following procedure.

To 1333 g of silica sol containing 30% by mass of $SiO_2$ and having pH=8.00, 50.0 g of oxalic acid dihydrate (purity of 99.5%) dissolved in 200 g of water was added (in the precursor slurry, 0.076 mol equivalents based on the sum of the metal elements). The pH was measured with a pH recording meter (DKK-TOA CORPORATION, HM-30P). The rate of addition on that occasion was 12 g/sec. On that occasion, the pH of the silica-oxalic acid mixed liquid was 1.10. The silica-oxalic acid mixed liquid was mixed at 0.2 kW/m$^3$ and 40° C. for 10 minutes. Subsequently, to the silica-oxalic acid mixed liquid, 483.7 g of ammonium paramolybdate [$(NH_4)_6Mo_7O_{24}.4H_2O$] dissolved in 869.5 g of water was added under stirring, and further 29.4 g of bismuth nitrate [$Bi(NO_3)_3.5H_2O$], 88.0 g of iron nitrate [$Fe(NO_3)_3.9H_2O$], 444.5 g of cobalt nitrate [$Co(NO_3)_2.6H_2O$], 195.9 g of nickel nitrate [$Ni(NO_3)_2.6H_2O$], 17.6 g of cerium nitrate [$Ce(NO_3)_3.6H_2O$], and 4.31 g of rubidium nitrate [$RbNO_3$] dissolved in 396.8 g of 16.6% by mass of nitric acid were added to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 595° C. for 2 hours to obtain a catalyst.

Example 25

A catalyst was produced in the same manner as in Example 24 except that the pH of the silica sol is 9.00, the amount of oxalic acid dihydrate is 25.0 g (in the precursor slurry, 0.038 mol equivalents based on the sum of the metal elements), and the pH of the silica-oxalic acid mixed liquid is 1.65.

Example 26

A catalyst was produced in the same manner as in Example 24 except that the pH of the silica sol is 9.70, the amount of oxalic acid dihydrate is 25.0 g (in the precursor slurry, 0.038 mol equivalents based on the sum of the metal elements), and the pH of the silica-oxalic acid mixed liquid is 5.30.

Example 27

A catalyst was produced in the same manner as in Example 24 except that the pH of the silica sol is 10.13, the amount of oxalic acid dihydrate is 25.0 g (in the precursor slurry, 0.038 mol equivalents based on the sum of the metal elements), and the pH of the silica-oxalic acid mixed liquid is 8.00.

Example 28

A catalyst in which a metal oxide having a composition represented by $Mo_{12.00}Bi_{0.82}Fe_{1.45}Co_{8.14}Ce_{0.55}Rb_{0.13}$ is carried on 40% by mass of silica was produced according to the following procedure.

To 1333 g of silica sol containing 30% by mass of $SiO_2$ and having pH=9.00, 25.0 g of oxalic acid dihydrate (purity of 99.5%) dissolved in 200 g of water was added (in the precursor slurry, 0.039 mol equivalents based on the sum of the metal elements). The pH was measured with a pH recording meter (DKK-TOA CORPORATION, HM-30P). The rate of addition on that occasion was 12 g/sec. On that occasion, the pH of the silica-oxalic acid mixed liquid was 1.65. The silica-oxalic acid mixed liquid was mixed at 0.2 kW/m$^3$ and 40° C. for 10 minutes. Subsequently, to the silica-oxalic acid mixed liquid, 462.7 g of ammonium paramolybdate [$(NH_4)_6Mo_7O_{24}.4H_2O$] dissolved in 855.9 g of water was added under stirring, and further 88.5 g of bismuth nitrate [$Bi(NO_3)_3.5H_2O$], 128.2 g of iron nitrate [$Fe(NO_3)_3.9H_2O$], 517.3 g of cobalt nitrate [$Co(NO_3)_2.6H_2O$], 52.4 g of cerium nitrate [$Ce(NO_3)_3.6H_2O$], and 4.06 g of rubidium nitrate [$RbNO_3$] dissolved in 391.1 g of 16.6% by mass of nitric acid were added to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 585° C. for 2 hours to obtain a catalyst.

Example 29

A catalyst in which a metal oxide having a composition represented by $Mo_{12.00}Bi_{1.05}Fe_{1.40}Co_{8.15}Ce_{0.70}Rb_{0.13}$ is carried on 40% by mass of silica was produced according to the following procedure.

To 1333 g of silica sol containing 30% by mass of $SiO_2$ and having pH=9.00, 25.0 g of oxalic acid dihydrate (purity of 99.5%) dissolved in 200 g of water was added (in the precursor slurry, 0.040 mol equivalents based on the sum of the metal elements). The pH was measured with a pH recording meter (DKK-TOA CORPORATION, HM-30P). The rate of addition on that occasion was 12 g/sec. On that occasion, the pH of the silica-oxalic acid mixed liquid was 1.65. The silica-oxalic acid mixed liquid was mixed at 0.2 kW/m$^3$ and 40° C. for 10 minutes. Subsequently, to the silica-oxalic acid mixed liquid, 450.8 g of ammonium paramolybdate [$(NH_4)_6Mo_7O_{24}.4H_2O$] dissolved in 810.3 g of water was added under stirring, and further 108.1 g of bismuth nitrate [$Bi(NO_3)_3.5H_2O$], 120.1 g of iron nitrate [$Fe(NO_3)_3.9H_2O$], 504.7 g of cobalt nitrate [$Co(NO_3)_2.6H_2O$], 64.5 g of cerium nitrate [$Ce(NO_3)_3.6H_2O$], and 3.96 g of rubidium nitrate [$RbNO_3$] dissolved in 388.6 g of 16.6% by mass of nitric acid were added to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 585° C. for 2 hours to obtain a catalyst.

Example 30

A catalyst in which a metal oxide having a composition represented by $Mo_{12.00}Bi_{0.27}Fe_{0.95}Co_{8.16}Ni_{1.48}Ce_{0.18}Rb_{0.13}$ is carried on 40% by mass of silica was produced according to the following procedure.

To 1333 g of silica sol containing 30% by mass of $SiO_2$ and having pH=9.00, 25.0 g of oxalic acid dihydrate (purity of 99.5%) dissolved in 200 g of water was added (in the precursor slurry, 0.038 mol equivalents based on the sum of the metal elements). The pH was measured with a pH recording meter (DKK-TOA CORPORATION, HM-30P). The rate of addition on that occasion was 12 g/sec. On that occasion, the pH of the silica-oxalic acid mixed liquid was 1.65. The silica-oxalic acid mixed liquid was mixed at 0.2 kW/m$^3$ and 40° C. for 10 minutes. Subsequently, to the silica-oxalic acid mixed liquid, 483.7 g of ammonium paramolybdate [$(NH_4)_6Mo_7O_{24}.4H_2O$] dissolved in 869.4 g of water was added under stirring, and further 29.4 g of bismuth nitrate [$Bi(NO_3)_3.5H_2O$], 88.0 g of iron nitrate [$Fe(NO_3)_3.9H_2O$], 542.5 g of cobalt nitrate [$Co(NO_3)_2.6H_2O$], 98.0 g of nickel nitrate [$Ni(NO_3)_2.6H_2O$], 17.6 g of cerium nitrate [$Ce(NO_3)_3.6H_2O$], and 4.31 g of rubidium nitrate [$RbNO_3$] dissolved in 396.7 g of 16.6% by mass of nitric acid were added to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 585° C. for 2 hours to obtain a catalyst.

Example 31

A catalyst in which a metal oxide having a composition represented by $Mo_{12.00}Bi_{0.27}Fe_{0.95}Co_{7.67}Ni_{1.97}Ce_{0.18}Rb_{0.13}$ is carried on 40% by mass of silica was produced according to the following procedure.

To 1333 g of silica sol containing 30% by mass of $SiO_2$ and having pH=9.00, 25.0 g of oxalic acid dihydrate (purity of 99.5%) dissolved in 200 g of water was added (in the precursor slurry, 0.038 mol equivalents based on the sum of the metal elements). The pH was measured with a pH recording meter (DKK-TOA CORPORATION, HM-30P). The rate of addition on that occasion was 12 g/sec. On that occasion, the pH of the silica-oxalic acid mixed liquid was 1.65. The silica-oxalic acid mixed liquid was mixed at 0.2 kW/m$^3$ and 40° C. for 10 minutes. Subsequently, to the silica-oxalic acid mixed liquid, 483.7 g of ammonium paramolybdate [$(NH_4)_6Mo_7O_{24}.4H_2O$] dissolved in 869.4 g of water was added under stirring, and further 29.4 g of bismuth nitrate [$Bi(NO_3)_3.5H_2O$], 88.0 g of iron nitrate

[Fe(NO$_3$)$_3$.9H$_2$O], 509.9 g of cobalt nitrate [Co(NO$_3$)$_2$.6H$_2$O], 130.6 g of nickel nitrate [Ni(NO$_3$)$_2$.6H$_2$O], 17.6 g of cerium nitrate [Ce(NO$_3$)$_3$.6H$_2$O], and 4.31 g of rubidium nitrate [RbNO$_3$] dissolved in 396.8 g of 16.6% by mass of nitric acid were added to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 590° C. for 2 hours to obtain a catalyst.

Comparative Example 1

A catalyst in which a metal oxide having a composition represented by Mo$_{12.00}$Bi$_{0.50}$Fe$_{1.31}$Co$_{4.05}$Ni$_{3.10}$Ce$_{0.87}$Rb$_{0.10}$K$_{0.08}$ is carried on 40% by mass of silica was produced according to the following procedure.

To 1333 g of silica sol containing 30% by mass of SiO$_2$, 481.6 g of ammonium paramolybdate [(NH$_4$)$_6$Mo$_7$O$_{24}$.4H$_2$O] dissolved in 865.8 g of water was added under stirring, and further 55.1 g of bismuth nitrate [Bi(NO$_3$)$_3$.5H$_2$O], 120.3 g of iron nitrate [Fe(NO$_3$)$_3$.9H$_2$O], 268.0 g of cobalt nitrate [Co(NO$_3$)$_2$.6H$_2$O], 204.9 g of nickel nitrate [Ni(NO$_3$)$_2$.6H$_2$O], 85.9 g of cerium nitrate [Ce(NO$_3$)$_3$.6H$_2$O], 3.35 g of rubidium nitrate [RbNO$_3$], and 1.84 g of potassium nitrate [KNO$_3$] dissolved in 391.8 g of 16.6% by mass of nitric acid were added to prepare a starting material slurry. Thereafter, 25.0 g of oxalic acid dihydrate (purity of 99.5%) dissolved in 200 g of water was added (in the precursor slurry, 0.040 mol equivalents based on the sum of the metal elements) to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried particle was held at 200° C. for 5 minutes, the temperature was then raised from 200° C. to 450° C. at 2.5° C./min, and the dried particle was then held at 450° C. for 20 minutes to perform denitration. The resultant denitrated powder was calcined at 590° C. for 2 hours to obtain a catalyst.

Comparative Example 2

A catalyst was produced in the same manner as in Example 1 except that oxalic acid dihydrate was not added.

Comparative Example 3

A catalyst in which a metal oxide having a composition represented by Mo$_{12.00}$Bi$_{0.39}$Fe$_{1.60}$Ni$_{6.97}$Mg$_{0.77}$Ce$_{0.63}$Rb$_{0.17}$ is carried on 40% by mass of silica was produced according to the following procedure.

To 1333 g of silica sol containing 30% by mass of SiO$_2$, 485.9 g of ammonium paramolybdate [(NH$_4$)$_6$Mo$_7$O$_{24}$.4H$_2$O] dissolved in 873.5 g of water was added under stirring, and further 43.1 g of bismuth nitrate [Bi(NO$_3$)$_3$.5H$_2$O], 148.0 g of iron nitrate [Fe(NO$_3$)$_3$.9H$_2$O], 464.7 g of nickel nitrate [Ni(NO$_3$)$_2$.6H$_2$O], 45.5 g of magnesium nitrate [Mg(NO$_3$)$_2$.6H$_2$O], 62.6 g of cerium nitrate [Ce(NO$_3$)$_3$.6H$_2$O], and 5.89 g of rubidium nitrate [RbNO$_3$] dissolved in 396.7 g of 16.6% by mass of nitric acid were added to prepare a starting material slurry. Thereafter, 25.0 g of oxalic acid dihydrate (purity of 99.5%) dissolved in 200 g of water was added (in the precursor slurry, 0.038 mol equivalents based on the sum of the metal elements) to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried particle was held at 200° C. for 5 minutes, the temperature was then raised from 200° C. to 450° C. at 2.5° C./min., and the dried particle was then held at 450° C. for 20 minutes to perform denitration. The resultant denitrated powder was calcined at 580° C. for 2 hours to obtain a catalyst.

Comparative Example 4

A catalyst was produced in the same manner as in Example 6 except that oxalic acid dihydrate was not added.

Comparative Example 5

A catalyst in which a metal oxide having a composition represented by Mo$_{12.00}$Bi$_{1.20}$Fe$_{0.60}$Ni$_{7.80}$Cr$_{1.20}$K$_{0.48}$ is carried on 60% by mass of silica was produced according to the following procedure.

To 2000 g of silica sol containing 30% by mass of SiO$_2$, 308.0 g of ammonium paramolybdate [(NH$_4$)$_6$Mo$_7$O$_{24}$.4H$_2$O] dissolved in 553.7 g of water was added under stirring, and further 84.6 g of bismuth nitrate [Bi(NO$_3$)$_3$.5H$_2$O], 35.2 g of iron nitrate [Fe(NO$_3$)$_3$.9H$_2$O], 329.8 g of nickel nitrate [Ni(NO$_3$)$_2$.6H$_2$O], 69.8 g of chromium nitrate [Cr(NO$_3$)$_3$.9H$_2$O], and 7.06 g of potassium nitrate [KNO$_3$] dissolved in 387.6 g of 16.6% by mass of nitric acid were added to prepare a starting material slurry. Thereafter, 25.0 g of oxalic acid dihydrate (purity of 99.5%) dissolved in 200 g of water was added (in the precursor slurry, 0.059 mol equivalents based on the sum of the metal elements) to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried particle was held at 200° C. for 5 minutes, the temperature was then raised from 200° C. to 450° C. at 2.5° C./min, and the dried particle was then held at 450° C. for 20 minutes to perform denitration. The resultant denitrated powder was calcined at 590° C. for 2 hours to obtain a catalyst.

Comparative Example 6

A catalyst in which a metal oxide having a composition represented by Mo$_{12.00}$Bi$_{2.40}$Fe$_{2.40}$Ni$_{6.00}$Zn$_{1.80}$Ce$_{0.24}$K$_{0.24}$ is carried on 60% by mass of silica was produced according to the following procedure.

To 2000 g of silica sol containing 30% by mass of SiO$_2$, 271.3 g of ammonium paramolybdate [(NH$_4$)$_6$Mo$_7$O$_{24}$.4H$_2$O] dissolved in 487.7 g of water was added under stirring, and further 149.1 g of bismuth nitrate [Bi(NO$_3$)$_3$.5H$_2$O], 124.2 g of iron nitrate [Fe(NO$_3$)$_3$.9H$_2$O], 223.5 g of nickel nitrate [Ni(NO$_3$)$_2$.6H$_2$O], 68.6 g of zinc nitrate [Zn(NO$_3$)$_2$.6H$_2$O], 13.3 g of cerium nitrate [Ce(NO$_3$)$_3$.6H$_2$O], and 3.11 g of potassium nitrate [$KNO_3$] dissolved in 382.2 g of 16.6% by mass of nitric acid were added to prepare a starting material slurry. Thereafter, 25.0 g of oxalic acid dihydrate (purity of 99.5%) dissolved in 200 g of water was added (in the precursor slurry, 0.061 mol equivalents based on the sum of the metal elements) to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried particle was held at 200° C. for 5 minutes, the temperature was then raised from 200° C. to 450° C. at 2.5° C./min, and the dried particle was then held at 450° C. for 20 minutes to perform denitration. The resultant denitrated powder was calcined at 570° C. for 2 hours to obtain a catalyst.

Comparative Example 7

A catalyst in which a metal oxide having a composition represented by $Mo_{12.00}Bi_{0.47}Fe_{1.35}Co_{4.15}Ni_{3.00}Ce_{0.91}Rb_{0.14}$ is carried on 40% by mass of silica was produced according to the following procedure.

To 1333 g of silica sol containing 30% by mass of $SiO_2$, 481.1 g of ammonium paramolybdate [$(NH_4)_6Mo_7O_{24}\cdot4H_2O$] dissolved in 864.9 g of water was added under stirring, and further 51.8 g of bismuth nitrate [$Bi(NO_3)_3\cdot5H_2O$], 123.9 g of iron nitrate [$Fe(NO_3)_3\cdot9H_2O$], 274.4 g of cobalt nitrate [$Co(NO_3)_2\cdot6H_2O$], 198.1 g of nickel nitrate [$Ni(NO_3)_2\cdot6H_2O$], 89.7 g of cerium nitrate [$Ce(NO_3)_3\cdot6H_2O$], and 4.81 g of rubidium nitrate [$RbNO_3$] dissolved in 392.0 g of 16.6% by mass of nitric acid were added to prepare a starting material slurry. Thereafter, 25.0 g of oxalic acid dihydrate (purity of 99.5%) dissolved in 200 g of water was added (in the precursor slurry, 0.040 mol equivalents based on the sum of the metal elements) to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried particle was held at 200° C. for 5 minutes, the temperature was then raised from 200° C. to 450° C. at 2.5° C./min, and the dried particle was then held at 450° C. for 20 minutes to perform denitration. The resultant denitrated powder was calcined at 590° C. for 2 hours to obtain a catalyst.

Comparative Example 8

A catalyst in which a metal oxide having a composition represented by $Mo_{12.00}Bi_{0.57}Fe_{1.01}Co_{6.83}Ni_{0.98}Mg_{0.98}Ce_{0.38}Rb_{0.12}$ is carried on 40% by mass of silica was produced according to the following procedure.

To 1333 g of silica sol containing 30% by mass of $SiO_2$ and having pH=9.00, 482.0 g of ammonium paramolybdate [$(NH_4)_6Mo_7O_{24}\cdot4H_2O$] dissolved in 866.4 g of water was added under stirring, and further 62.7 g of bismuth nitrate [$Bi(NO_3)_3\cdot5H_2O$], 93.0 g of iron nitrate [$Fe(NO_3)_3\cdot9H_2O$], 452.3 g of cobalt nitrate [$Co(NO_3)_2\cdot6H_2O$], 64.5 g of nickel nitrate [$Ni(NO_3)_2\cdot6H_2O$], 56.9 g of magnesium nitrate [$Mg(NO_3)_2\cdot6H_2O$], 37.4 g of cerium nitrate [$Ce(NO_3)_3\cdot6H_2O$], and 3.93 g of rubidium nitrate [$RbNO_3$] dissolved in 395.2 g of 16.6% by mass of nitric acid were added to prepare a starting material slurry. Thereafter, 25.0 g of oxalic acid dihydrate (purity of 99.5%) dissolved in 200 g of water was added (in the precursor slurry, 0.038 mol equivalents based on the sum of the metal elements) to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried particle was held at 200° C. for 5 minutes, the temperature was then raised from 200° C. to 450° C. at 2.5° C./min, and the dried particle was then held at 450° C. for 20 minutes to perform denitration. The resultant denitrated powder was calcined at 590° C. for 2 hours to obtain a catalyst.

Comparative Example 9

A catalyst was produced in the same manner as in Comparative Example 8 except that oxalic acid dihydrate was not added.

Comparative Example 10

A catalyst in which a metal oxide having a composition represented by $Mo_{12.00}Bi_{0.57}Fe_{1.01}Co_{2.24}Ni_{6.54}Ce_{0.38}Rb_{0.12}$ is carried on 40% by mass of silica was produced according to the following procedure.

To 1333 g of silica sol containing 30% by mass of $SiO_2$ and having pH=9.00, 479.5 g of ammonium paramolybdate [$(NH_4)_6Mo_7O_{24}\cdot4H_2O$] dissolved in 855.9 g of water was added under stirring, and further 61.9 g of bismuth nitrate [$Bi(NO_3)_3\cdot5H_2O$], 91.9 g of iron nitrate [$Fe(NO_3)_3\cdot9H_2O$], 146.8 g of cobalt nitrate [$Co(NO_3)_2\cdot6H_2O$], 427.2 g of nickel nitrate [$Ni(NO_3)_2\cdot6H_2O$], 36.9 g of cerium nitrate [$Ce(NO_3)_3\cdot6H_2O$], and 3.88 g of rubidium nitrate [$RbNO_3$] dissolved in 393.2 g of 16.6% by mass of nitric acid were added to prepare a starting material slurry. Thereafter, 25.0 g of oxalic acid dihydrate (purity of 99.5%) dissolved in 200 g of water was added (in the precursor slurry, 0.039 mol equivalents based on the sum of the metal elements) to prepare a precursor slurry. Subsequently, the precursor slurry was dried using a rotary disk type spray drier. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried particle was held at 200° C. for 5 minutes, the temperature was then raised from 200° C. to 450° C. at 2.5° C./min, and the dried particle was then held at 450° C. for 20 minutes to perform denitration. The resultant denitrated powder was calcined at 600° C. for 2 hours to obtain a catalyst.

Comparative Example 11

A catalyst was produced in the same manner as in Comparative Example 10 except that oxalic acid dihydrate was not added.

Comparative Example 12

A catalyst in which a metal oxide having a composition represented by $Mo_{12.00}Bi_{0.84}Fe_{2.06}Co_{6.67}Ce_{0.56}Rb_{0.12}$ is carried on 40% by mass of silica was produced according to the following procedure.

To 1333 g of silica sol containing 30% by mass of $SiO_2$ and having pH=9.00, 472.5 g of ammonium paramolybdate $[(NH_4)_6Mo_7O_{24} \cdot 4H_2O]$ dissolved in 849.4 g of water was added under stirring, and further 90.7 g of bismuth nitrate $[Bi(NO_3)_3 \cdot 5H_2O]$, 185.4 g of iron nitrate $[Fe(NO_3)_3 \cdot 9H_2O]$, 432.8 g of cobalt nitrate $[Co(NO_3)_2 \cdot 6H_2O]$, 54.4 g of cerium nitrate $[Ce(NO_3)_3 \cdot 6H_2O]$, and 3.96 g of rubidium nitrate $[RbNO_3]$ dissolved in 391.6 g of 16.6% by mass of nitric acid were added to prepare a starting material slurry. Thereafter, 25.0 g of oxalic acid dihydrate (purity of 99.5%) dissolved in 200 g of water was added (in the precursor slurry, 0.040 mol equivalents based on the sum of the metal elements) to prepare a starting material slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried particle was held at 200° C. for 5 minutes, the temperature was then raised from 200° C. to 450° C. at 2.5° C./min, and the dried particle was then held at 450° C. for 20 minutes to perform denitration. The resultant denitrated powder was calcined at 580° C. for 2 hours to obtain a catalyst.

Comparative Example 13

A catalyst was produced in the same manner as in Comparative Example 12 except that oxalic acid dihydrate was not added.

Comparative Example 14

A catalyst in which a metal oxide having a composition represented by $Mo_{12.00}Bi_{0.27}Fe_{0.95}Co_{6.69}Ni_{2.95}Ce_{0.18}Rb_{0.13}$ is carried on 40% by mass of silica was produced according to the following procedure.

To 1333 g of silica sol containing 30% by mass of $SiO_2$ and having pH=9.00, 483.7 g of ammonium paramolybdate $[(NH_4)_6Mo_7O_{24} \cdot 4H_2O]$ dissolved in 869.5 g of water was added under stirring, and further 29.4 g of bismuth nitrate $[Bi(NO_3)_3 \cdot 5H_2O]$, 88.0 g of iron nitrate $[Fe(NO_3)_3 \cdot 9H_2O]$, 444.5 g of cobalt nitrate $[Co(NO_3)_2 \cdot 6H_2O]$, 195.9 g of nickel nitrate $[Ni(NO_3)_2 \cdot 6H_2O]$, 17.6 g of cerium nitrate $[Ce(NO_3)_3 \cdot 6H_2O]$, and 4.31 g of rubidium nitrate $[RbNO_3]$ dissolved in 396.8 g of 16.6% by mass of nitric acid were added to prepare a starting material slurry. Thereafter, 25.0 g of oxalic acid dihydrate (purity of 99.5%) dissolved in 200 g of water was added (in the precursor slurry, 0.038 mol equivalents based on the sum of the metal elements) to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried particle was held at 200° C. for 5 minutes, the temperature was then raised from 200° C. to 450° C. at 2.5° C./min, and the dried particle was then held at 450° C. for 20 minutes to perform denitration. The resultant denitrated powder was calcined at 595° C. for 2 hours to obtain a catalyst.

Comparative Example 15

A catalyst was produced in the same manner as in Comparative Example 14 except that oxalic acid dihydrate was not added.

Comparative Example 16

A catalyst in which a metal oxide having a composition represented by $Mo_{12.00}Bi_{0.82}Fe_{1.45}Co_{8.14}Ce_{0.55}Rb_{0.13}$ is carried on 40% by mass of silica was produced according to the following procedure.

To 1333 g of silica sol containing 30% by mass of $SiO_2$ and having pH=9.00, 462.7 g of ammonium paramolybdate $[(NH_4)_6Mo_7O_{24} \cdot 4H_2O]$ dissolved in 855.9 g of water was added under stirring, and further 88.5 g of bismuth nitrate $[Bi(NO_3)_3 \cdot 5H_2O]$, 128.2 g of iron nitrate $[Fe(NO_3)_3 \cdot 9H_2O]$, 517.3 g of cobalt nitrate $[Co(NO_3)_2 \cdot 6H_2O]$, 52.4 g of cerium nitrate $[Ce(NO_3)_3 \cdot 6H_2O]$, and 4.06 g of rubidium nitrate $[RbNO_3]$ dissolved in 391.1 g of 16.6% by mass of nitric acid were added to prepare a starting material slurry. Thereafter, 25.0 g of oxalic acid dihydrate (purity of 99.5%) dissolved in 200 g of water was added (in the precursor slurry, 0.039 mol equivalents based on the sum of the metal elements) to prepare a precursor slurry. Subsequently, the precursor slurry was dried using a rotary disk type spray drier. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried particle was held at 200° C. for 5 minutes, the temperature was then raised from 200° C. to 450° C. at 2.5° C./min, and the dried particle was then held at 450° C. for 20 minutes to perform denitration. The resultant denitrated powder was calcined at 585° C. for 2 hours to obtain a catalyst.

Comparative Example 17

A catalyst in which a metal oxide having a composition represented by $Mo_{12.00}Bi_{1.05}Fe_{1.40}Co_{8.15}Ce_{0.70}Rb_{0.13}$ is carried on 40% by mass of silica was produced according to the following procedure.

To 1333 g of silica sol containing 30% by mass of $SiO_2$ and having pH=9.00, 450.8 g of ammonium paramolybdate $[(NH_4)_6Mo_7O_{24} \cdot 4H_2O]$ dissolved in 810.3 g of water was added under stirring, and further 108.1 g of bismuth nitrate $[Bi(NO_3)_3 \cdot 5H_2O]$, 120.1 g of iron nitrate $[Fe(NO_3)_3 \cdot 9H_2O]$, 504.7 g of cobalt nitrate $[Co(NO_3)_2 \cdot 6H_2O]$, 64.5 g of cerium nitrate $[Ce(NO_3)_3 \cdot 6H_2O]$, and 3.96 g of rubidium nitrate $[RbNO_3]$ dissolved in 388.6 g of 16.6% by mass of nitric acid were added to prepare a starting material slurry. Thereafter, 25.0 g of oxalic acid dihydrate (purity of 99.5%) dissolved in 200 g of water was added (in the precursor slurry, 0.040 mol equivalents based on the sum of the metal elements) to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried particle was held at 200° C. for 5 minutes, the temperature was then raised from 200° C. to 450° C. at 2.5° C./min, and the dried particle was then held at 450° C. for 20 minutes to perform denitration. The resultant denitrated powder was calcined at 585° C. for 2 hours to obtain a catalyst.

Comparative Example 18

A catalyst in which a metal oxide having a composition represented by $Mo_{12.00}Bi_{0.27}Fe_{0.95}Co_{8.16}Ni_{1.48}Ce_{0.18}Rb_{0.13}$ is carried on 40% by mass of silica was produced according to the following procedure.

To 1333 g of silica sol containing 30% by mass of $SiO_2$ and having pH=9.00, 483.7 g of ammonium paramolybdate [$(NH_4)_6Mo_7O_{24}\cdot 4H_2O$] dissolved in 869.4 g of water was added under stirring, and further 29.4 g of bismuth nitrate [$Bi(NO_3)_3\cdot 5H_2O$], 88.0 g of iron nitrate [$Fe(NO_3)_3\cdot 9H_2O$], 542.5 g of cobalt nitrate [$Co(NO_3)_2\cdot 6H_2O$], 98.0 g of nickel nitrate [$Ni(NO_3)_2\cdot 6H_2O$], 17.6 g of cerium nitrate [$Ce(NO_3)_3\cdot 6H_2O$], and 4.31 g of rubidium nitrate [$RbNO_3$] dissolved in 396.7 g of 16.6% by mass of nitric acid were added to prepare a starting material slurry. Thereafter, 25.0 g of oxalic acid dihydrate (purity of 99.5%) dissolved in 200 g of water was added (in the precursor slurry, 0.038 mol equivalents based on the sum of the metal elements) to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried particle was held at 200° C. for 5 minutes, the temperature was then raised from 200° C. to 450° C. at 2.5° C./min, and the dried particle was then held at 450° C. for 20 minutes to perform denitration. The resultant denitrated powder was calcined at 585° C. for 2 hours to obtain a catalyst.

Comparative Example 19

A catalyst in which a metal oxide having a composition represented by $Mo_{12.00}Bi_{0.27}Fe_{0.95}Co_{7.67}Ni_{1.97}Ce_{0.18}Rb_{0.13}$ is carried on 40% by mass of silica was produced according to the following procedure.

To 1333 g of silica sol containing 30% by mass of $SiO_2$ and having pH=9.00, 483.7 g of ammonium paramolybdate [$(NH_4)_6Mo_7O_{24}\cdot 4H_2O$] dissolved in 869.4 g of water was added under stirring, and further 29.4 g of bismuth nitrate [$Bi(NO_3)_3\cdot 5H_2O$], 88.0 g of iron nitrate [$Fe(NO_3)_3\cdot 9H_2O$], 509.9 g of cobalt nitrate [$Co(NO_3)_2\cdot 6H_2O$], 130.6 g of nickel nitrate [$Ni(NO_3)_2\cdot 6H_2O$], 17.6 g of cerium nitrate [$Ce(NO_3)_3\cdot 6H_2O$], and 4.31 g of rubidium nitrate [$RbNO_3$] dissolved in 396.8 g of 16.6% by mass of nitric acid were added to prepare a precursor slurry. Thereafter, 25.0 g of oxalic acid dihydrate (purity of 99.5%) dissolved in 200 g of water was added (in the precursor slurry, 0.038 mol equivalents based on the sum of the metal elements) to prepare a precursor slurry. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried particle was held at 200° C. for 5 minutes, the temperature was then raised from 200° C. to 450° C. at 2.5° C./min, and the dried particle was then held at 450° C. for 20 minutes to perform denitration. The resultant denitrated powder was calcined at 590° C. for 2 hours to obtain a catalyst.

Production conditions for the catalysts obtained in Examples 1 to 31 and Comparative Examples 1 to 19 and the compositions of the catalysts are shown in Table 1.

TABLE 1

| | Timing of adding carboxylic acid | pH Silica sol | pH Silica-carboxylic acid mixed liquid | Amount of carboxylic acid Mol equivalents based on the sum of metal elements | Time of stirring silica-carboxylic acid min | Rate of addition of carboxylic acid* g/sec. | Mo | Bi | Fe | Co | Ni | X Mg | Zn | Ce | Y Cr | Rb | Z K |
|---|---|---|---|---|---|---|---|---|---|---|---|---|---|---|---|---|---|
| Example 1 | Silica sol | 9.00 | 1.65 | 0.040 | 10 | 12 | 12.00 | 0.50 | 1.31 | 4.05 | 3.10 | — | — | 0.87 | — | 0.10 | 0.08 |
| Example 2 | Silica sol | 9.00 | 1.65 | 0.040 | 30 | 12 | 12.00 | 0.50 | 1.31 | 4.05 | 3.10 | — | — | 0.87 | — | 0.10 | 0.08 |
| Example 3 | Silica sol | 9.00 | 1.65 | 0.040 | 80 | 12 | 12.00 | 0.50 | 1.31 | 4.05 | 3.10 | — | — | 0.87 | — | 0.10 | 0.08 |
| Example 4 | Silica sol | 9.00 | 1.65 | 0.040 | 10 | 8 | 12.00 | 0.50 | 1.31 | 4.05 | 3.10 | — | — | 0.87 | — | 0.10 | 0.08 |
| Example 5 | Silica sol | 9.00 | 1.65 | 0.040 | 10 | 3 | 12.00 | 0.50 | 1.31 | 4.05 | 3.10 | — | — | 0.87 | — | 0.10 | 0.08 |
| Example 6 | Silica sol | 9.00 | 1.65 | 0.038 | 10 | 12 | 12.00 | 0.39 | 1.60 | — | 6.97 | 0.77 | — | 0.63 | — | 0.17 | — |
| Example 7 | Silica sol | 9.00 | 1.65 | 0.038 | 80 | 12 | 12.00 | 0.39 | 1.60 | — | 6.97 | 0.77 | — | 0.63 | — | 0.17 | — |
| Example 8 | Silica sol | 9.00 | 1.65 | 0.038 | 10 | 3 | 12.00 | 0.39 | 1.60 | — | 6.97 | 0.77 | — | 0.63 | — | 0.17 | — |
| Example 9 | Silica sol | 9.00 | 1.65 | 0.059 | 10 | 12 | 12.00 | 1.20 | 0.60 | — | 7.80 | — | — | — | — | — | 0.48 |
| Example 10 | Silica sol | 9.00 | 1.76 | 0.061 | 10 | 12 | 12.00 | 2.40 | 2.40 | — | 6.00 | — | 1.80 | 0.24 | — | 0.14 | 0.24 |
| Example 11 | Silica sol | 9.00 | 1.76 | 0.040 | 10 | 12 | 12.00 | 0.47 | 1.35 | 4.15 | 3.00 | — | — | 0.91 | — | 0.12 | — |
| Example 12 | Silica sol | 9.00 | 1.65 | 0.076 | 10 | 12 | 12.00 | 0.57 | 1.01 | 6.83 | 0.98 | 0.98 | — | 0.38 | — | 0.12 | — |
| Example 13 | Silica sol | 8.00 | 1.10 | 0.038 | 10 | 12 | 12.00 | 0.57 | 1.01 | 6.83 | 0.98 | 0.98 | — | 0.38 | — | 0.12 | — |
| Example 14 | Silica sol | 9.70 | 5.30 | 0.038 | 10 | 12 | 12.00 | 0.57 | 1.01 | 6.83 | 0.98 | 0.98 | — | 0.38 | — | 0.12 | — |
| Example 15 | Silica sol | 10.13 | 8.00 | 0.038 | 10 | 12 | 12.00 | 0.57 | 1.01 | 6.83 | 0.98 | 0.98 | — | 0.38 | — | 0.12 | — |
| Example 16 | Silica sol | 8.00 | 1.10 | 0.077 | 10 | 12 | 12.00 | 0.57 | 1.01 | 2.24 | 6.54 | — | — | 0.38 | — | 0.12 | — |
| Example 17 | Silica sol | 9.00 | 1.65 | 0.039 | 10 | 12 | 12.00 | 0.57 | 1.01 | 2.24 | 6.54 | — | — | 0.38 | — | 0.12 | — |
| Example 18 | Silica sol | 9.70 | 5.30 | 0.039 | 10 | 12 | 12.00 | 0.57 | 1.01 | 2.24 | 6.54 | — | — | 0.38 | — | 0.12 | — |
| Example 19 | Silica sol | 10.13 | 8.00 | 0.039 | 10 | 12 | 12.00 | 0.57 | 1.01 | 2.24 | 6.54 | — | — | 0.38 | — | 0.12 | — |
| Example 20 | Silica sol | 8.00 | 1.10 | 0.080 | 10 | 12 | 12.00 | 0.84 | 2.06 | 6.67 | — | — | — | 0.56 | — | 0.12 | — |
| Example 21 | Silica sol | 9.00 | 1.65 | 0.040 | 10 | 12 | 12.00 | 0.84 | 2.06 | 6.67 | — | — | — | 0.56 | — | 0.12 | — |
| Example 22 | Silica sol | 9.70 | 5.30 | 0.040 | 10 | 12 | 12.00 | 0.84 | 2.06 | 6.67 | — | — | — | 0.56 | — | 0.12 | — |
| Example 23 | Silica sol | 10.13 | 8.00 | 0.040 | 10 | 12 | 12.00 | 0.84 | 2.06 | 6.67 | — | — | — | 0.56 | — | 0.12 | — |
| Example 24 | Silica sol | 8.00 | 1.10 | 0.075 | 10 | 12 | 12.00 | 0.27 | 0.95 | 6.69 | 2.95 | — | — | 0.18 | — | 0.13 | — |
| Example 25 | Silica sol | 9.00 | 1.65 | 0.038 | 10 | 12 | 12.00 | 0.27 | 0.95 | 6.69 | 2.95 | — | — | 0.18 | — | 0.13 | — |
| Example 26 | Silica sol | 9.70 | 5.30 | 0.038 | 10 | 12 | 12.00 | 0.27 | 0.95 | 6.69 | 2.95 | — | — | 0.18 | — | 0.13 | — |
| Example 27 | Silica sol | 10.13 | 8.00 | 0.038 | 10 | 12 | 12.00 | 0.27 | 0.95 | 6.69 | 2.95 | — | — | 0.18 | — | 0.13 | — |
| Example 28 | Silica sol | 9.00 | 1.65 | 0.039 | 10 | 12 | 12.00 | 0.82 | 1.45 | 8.14 | — | — | — | 0.55 | — | 0.13 | — |
| Example 29 | Silica sol | 9.00 | 1.65 | 0.040 | 10 | 12 | 12.00 | 1.05 | 1.40 | 8.15 | — | — | — | 0.70 | — | 0.13 | — |
| Example 30 | Silica sol | 9.00 | 1.65 | 0.038 | 10 | 12 | 12.00 | 0.27 | 0.95 | 8.16 | 1.48 | — | — | 0.18 | — | 0.13 | — |
| Example 31 | Silica sol | 9.00 | 1.65 | 0.038 | 10 | 12 | 12.00 | 0.27 | 0.95 | 7.67 | 1.97 | — | — | 0.18 | — | 0.13 | — |

TABLE 1-continued

| | Timing of adding carboxylic acid | pH Silica sol | pH Silica-carboxylic acid mixed liquid | Amount of carboxylic acid Mol equivalents based on the sum of metal elements | Time of stirring silica-carboxylic acid min | Rate of addition of carboxylic acid* g/sec. | Mo | Bi | Fe | Co | X Ni | X Mg | X Zn | Y Ce | Y Cr | Z Rb | Z K |
|---|---|---|---|---|---|---|---|---|---|---|---|---|---|---|---|---|---|
| Comparative Example 1 | Starting material slurry | 9.00 | — | 0.040 | — | — | 12.00 | 0.50 | 1.31 | 4.05 | 3.10 | — | — | 0.87 | — | 0.10 | 0.08 |
| Comparative Example 2 | Not added | 9.00 | — | — | — | — | 12.00 | 0.50 | 1.31 | 4.05 | 3.10 | — | — | 0.87 | — | 0.10 | 0.08 |
| Comparative Example 3 | Starting material slurry | 9.00 | — | 0.038 | — | — | 12.00 | 0.39 | 1.60 | — | 6.97 | 0.77 | — | 0.63 | — | 0.17 | — |
| Comparative Example 4 | Not added | 9.00 | — | — | — | — | 12.00 | 0.39 | 1.60 | — | 6.97 | 0.77 | — | 0.63 | — | 0.17 | — |
| Comparative Example 5 | Starting material slurry | 9.00 | — | 0.059 | — | — | 12.00 | 1.20 | 0.60 | — | 7.80 | — | — | — | 1.20 | — | 0.48 |
| Comparative Example 6 | Starting material slurry | 9.00 | — | 0.061 | — | — | 12.00 | 2.40 | 2.40 | — | 6.00 | — | — | 0.24 | — | — | 0.24 |
| Comparative Example 7 | Starting material slurry | 9.00 | — | 0.040 | — | — | 12.00 | 0.47 | 1.35 | 4.15 | 3.00 | — | — | 0.91 | — | 0.14 | — |
| Comparative Example 8 | Starting material slurry | 9.00 | — | 0.038 | — | — | 12.00 | 0.57 | 1.01 | 6.83 | 0.98 | 0.98 | — | 0.38 | — | 0.12 | — |
| Comparative Example 9 | Not added | 9.00 | — | — | — | — | 12.00 | 0.57 | 1.01 | 6.83 | 0.98 | 0.98 | — | 0.38 | — | 0.12 | — |
| Comparative Example 10 | Starting material slurry | 9.00 | — | 0.039 | — | — | 12.00 | 0.57 | 1.01 | 2.24 | 6.54 | — | — | 0.38 | — | 0.12 | — |
| Comparative Example 11 | Not added | 9.00 | — | — | — | — | 12.00 | 0.57 | 1.01 | 2.24 | 6.54 | — | — | 0.38 | — | 0.12 | — |
| Comparative Example 12 | Starting material slurry | 9.00 | — | 0.040 | — | — | 12.00 | 0.84 | 2.06 | 6.67 | — | — | — | 0.56 | — | 0.12 | — |
| Comparative Example 13 | Not added | 9.00 | — | — | — | — | 12.00 | 0.84 | 2.06 | 6.67 | — | — | — | 0.56 | — | 0.12 | — |
| Comparative Example 14 | Starting material slurry | 9.00 | — | 0.038 | — | — | 12.00 | 0.27 | 0.95 | 6.69 | 2.95 | — | — | 0.18 | — | 0.13 | — |
| Comparative Example 15 | Not added | 9.00 | — | — | — | — | 12.00 | 0.27 | 0.95 | 6.69 | 2.95 | — | — | 0.18 | — | 0.13 | — |
| Comparative Example 16 | Starting material slurry | 9.00 | — | 0.039 | — | — | 12.00 | 0.82 | 1.45 | 8.14 | — | — | — | 0.55 | — | 0.13 | — |
| Comparative Example 17 | Starting material slurry | 9.00 | — | 0.040 | — | — | 12.00 | 1.05 | 1.40 | 8.15 | — | — | — | 0.70 | — | 0.13 | — |
| Comparative Example 18 | Starting material slurry | 9.00 | — | 0.038 | — | — | 12.00 | 0.27 | 0.95 | 8.16 | 1.48 | — | — | 0.18 | — | 0.13 | — |
| Comparative Example 19 | Starting material slurry | 9.00 | — | 0.038 | — | — | 12.00 | 0.27 | 0.95 | 7.67 | 1.97 | — | — | 0.18 | — | 0.13 | — |

*Rate of addition to 1 kg of $SiO_2$

[Ammoxidation Reaction Conditions and Results]

A Pyrex (R) glass pipe having an inner diameter of 25 mm, the glass pipe having 16 10-mesh wire nets built-in at an interval of 1 cm, was used as a reaction pipe to be used for ammoxidation reaction of propylene. The amount of the catalyst was set to 50 cc, the reaction temperature was set to 430° C., the reaction pressure was set to 0.17 MPa, and a mixed gas (propylene, ammonia, oxygen, helium) comprising 9% by volume of propylene was passed through the glass pipe. The molar ratio of ammonia/propylene and the molar ratio of oxygen/propylene in each of Examples and Comparative Examples are set to the values shown in Table 2. The volume ratio of ammonia to propylene was set such that a sulfuric acid unit requirement defined by the following formula was 20±2 kg/T-AN. The volume ratio of oxygen to propylene was set such that an oxygen concentration of a gas at the outlet of the reactor was 0.2±0.02% by volume. In addition, the contact time defined by the following formula was changed by changing the flow rate of the mixed gas. The contact time was set such that the conversion rate of propylene, the conversion rate defined by the following formula, was thereby 99.3±0.2%. The yield of acrylonitrile produced through the reaction was determined as a value defined by the following formula.

$$\text{Sulfuric acid unit requirement}(kg/T-AN) = \frac{\text{Weight of sulfuric acid needed to neutralize unreacted ammonia (kg)}}{\text{Weight of acrylonitrile produced}(T)}$$

$$\text{Contact time(sec.)} = \frac{\text{Amount of catalyst}(cc)}{\text{Flow rate of mixed gas}(cc-NTP/\text{sec.})} \times$$

$$\frac{273}{273+\text{reaction temperature}(°C.)} \times \frac{\text{Reaction pressure}(MPa)}{0.10}$$

$$\text{Conversion rate of propylene}(\%) = \frac{\text{Propylene consumed(mol)}}{\text{Propylene supplied(mol)}} \times 100$$

$$\text{Acrylonitrile yield}(\%) = \frac{\text{Acrylonitrile produced(mol)}}{\text{Propylene supplied(mol)}} \times 100$$

[Measurement of Attrition Resistance Strength]

As the wear loss, the attrition resistance strength (attrition strength) for the catalysts was measured in accordance with the method described in "Test Method for Synthetic Fluid Cracking Catalyst" (American Cyanamid Co. Ltd. 6/31-4m-1/57) (hereinafter, referred to as "ACC method").

The attrition strength is evaluated as the wear loss, and the wear loss was determined as a value defined as described below.

$$\text{Wear loss }(\%) = R/(S-Q) \times 100$$

In the formula, Q represents a mass (g) of the catalyst scattering due to wear to an outside of a measurement system during the period from 0 to 5 hours, R represents a mass (g) of the catalyst scattering due to wear to the outside of the measurement system during the period from 5 to 20 hours, and S represents a mass (g) of the catalyst provided for the test.

The reaction conditions, the reaction results, and the attrition strength for the catalysts obtained in Examples and Comparative Examples are shown in Table 2. In Table 2, the "AN yield" represents the acrylonitrile yield, the "ATT strength" represents the attrition strength, and "-" herein means "not measured". It is to be noted that the reaction time was set to 20 hours. The wear loss (%) of a catalyst used for ammoxidation reaction in a fluidized bed is preferably 0 to 2.5%, more preferably 0 to 1.5%.

TABLE 2

|  | Ammonia/ propylene Molar ratio | Oxygen/ propylene Molar ratio | Contact time sec. | Conversion rate of propylene % | AN yield % | ATT strength % |
|---|---|---|---|---|---|---|
| Example 1 | 1.22 | 2.04 | 3.9 | 99.2 | 84.5 | 0.2 |
| Example 2 | 1.19 | 2.10 | 3.9 | 99.3 | 84.5 | 0.2 |
| Example 3 | 1.17 | 2.03 | 4.0 | 99.3 | 84.3 | 0.4 |
| Example 4 | 1.20 | 2.03 | 3.7 | 99.2 | 84.4 | 0.3 |
| Example 5 | 1.21 | 1.98 | 3.9 | 99.4 | 84.3 | 0.2 |
| Example 6 | 1.19 | 1.94 | 4.0 | 99.4 | 84.4 | 0.3 |
| Example 7 | 1.21 | 1.97 | 4.2 | 99.1 | 84.2 | 0.5 |
| Example 8 | 1.19 | 2.08 | 4.2 | 99.3 | 84.0 | 0.3 |
| Example 9 | 1.18 | 2.00 | 3.1 | 99.3 | 84.2 | — |
| Example 10 | 1.15 | 2.11 | 4.5 | 99.2 | 83.0 | — |
| Example 11 | 1.21 | 1.98 | 4.0 | 99.2 | 84.4 | 0.3 |
| Example 12 | 1.20 | 1.97 | 4.1 | 99.3 | 84.4 | 0.6 |
| Example 13 | 1.20 | 1.99 | 4.1 | 99.0 | 84.5 | 0.2 |
| Example 14 | 1.19 | 2.00 | 4.3 | 99.2 | 84.4 | 0.3 |
| Example 15 | 1.18 | 2.01 | 4.5 | 99.2 | 84.3 | 0.4 |
| Example 16 | 1.22 | 1.99 | 4.0 | 99.2 | 84.2 | 0.6 |
| Example 17 | 1.22 | 1.98 | 4.0 | 99.3 | 84.3 | 0.2 |
| Example 18 | 1.21 | 2.01 | 4.3 | 99.3 | 84.2 | 0.4 |
| Example 19 | 1.18 | 1.96 | 4.5 | 99.2 | 84.1 | 0.4 |
| Example 20 | 1.23 | 2.02 | 4.0 | 99.1 | 84.1 | 0.7 |
| Example 21 | 1.23 | 2.03 | 3.9 | 99.2 | 84.2 | 0.3 |
| Example 22 | 1.21 | 2.04 | 4.3 | 99.2 | 84.1 | 0.3 |
| Example 23 | 1.22 | 1.99 | 4.5 | 99.3 | 84.1 | 0.4 |
| Example 24 | 1.21 | 2.00 | 4.1 | 99.2 | 84.3 | 0.6 |
| Example 25 | 1.22 | 2.00 | 4.1 | 99.2 | 84.4 | 0.3 |
| Example 26 | 1.21 | 1.99 | 4.2 | 99.2 | 84.3 | 0.4 |
| Example 27 | 1.21 | 2.03 | 4.4 | 99.2 | 84.2 | 0.5 |
| Example 28 | 1.23 | 1.97 | 4.1 | 99.2 | 84.2 | 0.3 |
| Example 29 | 1.21 | 1.96 | 3.6 | 99.3 | 84.2 | 0.2 |
| Example 30 | 1.19 | 2.06 | 4.0 | 99.3 | 84.1 | 0.2 |
| Example 31 | 1.18 | 2.00 | 4.1 | 99.3 | 84.1 | 0.3 |

TABLE 2-continued

|  | Ammonia/propylene Molar ratio | Oxygen/propylene Molar ratio | Contact time sec. | Conversion rate of propylene % | AN yield % | ATT strength % |
|---|---|---|---|---|---|---|
| Comparative Example 1 | 1.18 | 1.90 | 3.8 | 99.2 | 84.2 | 0.2 |
| Comparative Example 2 | 1.15 | 1.88 | 4.1 | 99.3 | 83.7 | 0.4 |
| Comparative Example 3 | 1.17 | 1.96 | 4.1 | 99.3 | 83.8 | 0.3 |
| Comparative Example 4 | 1.15 | 1.95 | 4.2 | 99.4 | 83.5 | 0.2 |
| Comparative Example 5 | 1.16 | 2.05 | 3.5 | 99.1 | 83.8 | — |
| Comparative Example 6 | 1.13 | 2.13 | 4.7 | 99.3 | 82.7 | — |
| Comparative Example 7 | 1.19 | 2.05 | 4.2 | 99.3 | 84.0 | 0.2 |
| Comparative Example 8 | 1.19 | 2.00 | 4.1 | 99.2 | 84.0 | 0.2 |
| Comparative Example 9 | 1.19 | 2.03 | 4.2 | 99.2 | 83.4 | 0.2 |
| Comparative Example 10 | 1.20 | 2.00 | 4.0 | 99.2 | 83.9 | 0.2 |
| Comparative Example 11 | 1.20 | 2.02 | 4.1 | 99.2 | 83.3 | 0.2 |
| Comparative Example 12 | 1.21 | 2.05 | 3.9 | 99.3 | 83.8 | 0.2 |
| Comparative Example 13 | 1.21 | 2.07 | 4.1 | 99.2 | 83.3 | 0.2 |
| Comparative Example 14 | 1.20 | 2.03 | 4.2 | 99.1 | 84.0 | 0.2 |
| Comparative Example 15 | 1.20 | 2.04 | 4.3 | 99.2 | 83.5 | 0.2 |
| Comparative Example 16 | 1.20 | 1.97 | 4.2 | 99.2 | 84.0 | 0.3 |
| Comparative Example 17 | 1.19 | 1.98 | 3.7 | 99.2 | 84.0 | 0.3 |
| Comparative Example 18 | 1.18 | 2.05 | 4.0 | 99.2 | 83.9 | 0.3 |
| Comparative Example 19 | 1.17 | 2.02 | 4.2 | 99.2 | 83.9 | 0.3 |

As shown in Table 2, in the ammoxidation reaction of propylene using each catalyst produced according to the present embodiment, acrylonitrile can be obtained at a favorable yield.

Example 32

[Production of Catalyst 1]

A catalyst in which 60% by mass of a metal oxide produced by adjusting the mass of the starting materials added such that the composition of the metal oxide is made to be $Mo_{12}Bi_{0.25}Fe_{1.4}Ni_{3.0}Co_{5.8}Ce_{0.40}Rb_{0.12}O_f$ is carried on 40% by mass of silica was produced according to the following procedure.

A mixed liquid of two types of silica was obtained by mixing 666.7 g of aqueous silica sol containing 30% by mass of $SiO_2$ having an average particle diameter of primary particles of 12 nm and 500 g of aqueous silica sol containing 40% by mass of $SiO_2$ having an average particle diameter of primary particles of 41 nm.

Next, 320 g of 8% by mass of an oxalic acid aqueous solution was added to the mixed liquid of silica sol under stirring to obtain a first mixed liquid. Next, a liquid obtained by dissolving 486.2 g of ammonium paramolybdate [$(NH_4)_6Mo_7O_{24}.4H_2O$] in 870 g of water was added to the mixed liquid of silica sol (Mo-containing liquid; hereafter, referred to as "A1 liquid"). The whole amount of the A1 liquid was 2843 g.

Subsequently, in 400 g of a 16.6% by mass concentration nitric acid liquid, 28.09 g of bismuth nitrate [$Bi(NO_3)_3.5H_2O$], 131.1 g of iron nitrate [$Fe(NO_3)_3.9H_2O$], 202.9 g of nickel nitrate [$Ni(NO_3)_2.6H_2O$], 392.6 g of cobalt nitrate [$Co(NO_3)_2.6H_2O$], 39.62 g of cerium nitrate [$Ce(NO_3)_3.6H_2O$], and 4.038 g of rubidium nitrate [$RbNO_3$] were dissolved (Bi-containing liquid; hereafter, referred to as "B1 liquid"). The whole amount of the B1 liquid was 1198 g.

A container in which the A1 liquid was placed was connected to one inlet 1 of a vacant, Y-shaped stainless-steel cylinder pipe (inner diameter of 15 mm, length of 30 mm) (merging section) by piping (first flow channel) through a quantitative liquid feeding pump for the A1 liquid. In addition, a container in which the B1 liquid was placed was connected to the other inlet 2 of the Y-shaped pipe by piping (second flow channel) through a quantitative liquid feeding pump for the B1 liquid. The outlet of the Y-shaped pipe was connected to a stationary type mixer (static mixer) having a screw type interior material, and the outlet of the stationary type mixer was connected to a slurry-stirring tank having a stirrer by piping. FIG. 1 illustrates a schematic diagram of the apparatus.

The A1 liquid held at 40° C. and the B1 liquid held at 40° C. were simultaneously supplied to the Y-shaped pipe at a flow rate of 284 (g/min) using the quantitative liquid feeding pump for the A1 liquid and at a flow rate of 119 (g/min) using the quantitative liquid feeding pump for the B2 liquid, respectively, and the two liquids were contacted with each other in a parallel direction (parallel flow) in the Y-shaped pipe and the stationary type mixer. This operation was conducted for 10 minutes to prepare a MoBi-containing liquid being a slurry. The supply ratio of the B1 liquid [Bi-containing liquid] to the A1 liquid [Mo-containing liquid] during this operation was 119 (g/min)/284 (g/min)= 0.42, which was 1.0 times the mass ratio of the whole amount of the Bi-containing liquid to the whole amount of the Mo-containing liquid, 1198 (g)/2843 (g)=0.42. All (100% by mass) of the A1 liquid and the B1 liquid were merged at this supply ratio. The merging temperature during the operation was 40° C.

The whole amount of this MoBi-containing liquid was stored in the slurry-stirring tank provided at downstream from the stationary type mixer, and stirring was further continued at 40° C. for 1 hour after supplying the two liquids was completed. This MoBi-containing liquid had a pH of 1 or less and was in the form of a slurry before spray-drying.

Subsequently, this MoBi-containing liquid was spray-dried using a spray drier (manufactured by Ohkawara Kakohki Co., Ltd., model: OC-16) to obtain a dried powder. It is to be noted that the hot-air inlet temperature was set to 230° C., and the hot-air outlet temperature was set to 120° C.

Subsequently, preliminary calcination was applied to the dried catalyst precursor at 320° C. for 2 hours in an air atmosphere using an electric furnace, and final calcination was then applied at 600° C. for 2 hours in an air atmosphere to obtain a catalyst (catalyst 1).

The resultant catalyst 1 had a shape of a solid sphere and had an average particle diameter of 54 μm. The average particle diameter was measured using a laser diffraction/ scattering type particle size distribution measurement apparatus LA-300 manufactured by HORIBA, Ltd. It is to be noted that the average particle diameter of the catalysts in Examples and Reference Examples after this was also measured in the same manner and found to be 52 μm to 55 μm.

The concentration of Mo and the concentration of Bi on the surface of 100 particles of this catalyst 1 were measured with SEM-EDX to determine the ratio of the molar concentration of Bi to the molar concentration of Mo, $(Bi/Mo)_{surf}$. In addition, $(Bi/Mo)_{bulk}$ was determined from the bulk composition of the metal oxide, which is determined above, to determine the values $S_1 \ldots S_{100}$ obtained by dividing each $(Bi/Mo)_{surf}$ of 100 particles by $(Bi/Mo)_{bulk}$. Subsequently, the average value μ of those (the average value of $S_1 \ldots S_{100}$) was determined, and the standard deviation value was determined using the above-described formula (4). In addition, acrylonitrile was produced through ammoxidation reaction of propylene using the catalyst 1 to calculate the yield. The details on these measurement methods will be described later. The obtained results are shown in Table 4.

Example 33

[Production of Catalyst 2]

A catalyst in which 60% by mass of a metal oxide produced by adjusting the mass of the starting materials added such that the composition of the metal oxide is made to be $Mo_{12}Bi_{0.39}Fe_{1.60}Ni_{7.0}Mg_{0.77}Ce_{0.63}Rb_{0.17}O_f$ is carried on 40% by mass of silica was produced according to the following procedure.

First, to 1333 g of silica sol containing 30% by mass of $SiO_2$ having an average particle diameter of primary particles of 12 nm, 25.0 g of oxalic acid dihydrate dissolved in 200 g of water was added, and 485.9 g of ammonium paramolybdate $[(NH_4)_6Mo_7O_{24}\cdot 4H_2O]$ dissolved in 873.5 g of water was added under stirring to obtain a mixed liquid containing molybdenum and silica. Hereafter, this is referred to as A2 liquid. The whole amount of the A2 liquid was 2917 g.

Next, in 396.7 g of 16.6% by mass of nitric acid, 43.1 g of bismuth nitrate $[Bi(NO_3)_3\cdot 5H_2O]$, 148.0 g of iron nitrate $[Fe(NO_3)_3\cdot 9H_2O]$, 464.7 g of nickel nitrate $[Ni(NO_3)_2\cdot 6H_2O]$, 45.5 g of magnesium nitrate $[Mg(NO_3)_2\cdot 6H_2O]$, 62.6 g of cerium nitrate $[Ce(NO_3)_3\cdot 6H_2O]$, and 5.89 g of rubidium nitrate $[RbNO_3]$ were dissolved. Hereafter, this is referred to as B2 liquid. The whole amount of the B2 liquid was 1166 g.

In the same manner as in Example 32, the A2 liquid held at 40° C. and the B2 liquid held at 40° C. were contacted with each other in the same manner as in Example 32 at a flow rate of 291 (g/min) and at a flow rate of 117 (g/min), respectively. This operation was conducted for 10 minutes to prepare a MoBi-containing liquid being a slurry. The supply ratio of the B2 liquid [Bi-containing liquid] to the A2 liquid [Mo-containing liquid] during this operation was 117 (g/min)/291 (g/min)=0.40, which was 1.0 times the mass ratio of the whole amount of the Bi-containing liquid to the whole amount of the Mo-containing liquid, 1166 (g)/2917 (g)=0.40. All (100% by mass) of the A2 liquid and the B2 liquid were merged at this supply ratio. The merging temperature during the operation was 40° C.

The whole amount of this MoBi-containing liquid was stored in the slurry-stirring tank provided at downstream from the stationary type mixer, and stirring was further continued at 40° C. for 1 hour after supplying the two liquids was completed. This MoBi-containing liquid had a pH of 1 or less and was in the form of a slurry before spray-drying. Subsequently, this MoBi-containing liquid was spray-dried in the same manner as in Example 32 to obtain a dried powder. It is to be noted that the hot-air inlet temperature was set to 230° C., and the hot-air outlet temperature was set to 110° C.

Subsequently, preliminary calcination was applied to the dried catalyst precursor using an electric furnace such that the dried catalyst precursor was held at 200° C. for 5 minutes in an air atmosphere, the temperature was then raised from 200° C. to 450° C. at 2.5° C./min, and the dried catalyst precursor was then held at 450° C. for 20 minutes, and thereafter final calcination was applied at 580° C. for 2 hours in an air atmosphere to obtain a catalyst (catalyst 2).

The standard deviation value of the catalyst 2 obtained in the same manner as in Example 32 and the results of the ammoxidation reaction are shown in Table 4.

Example 34

A catalyst in which 58% by mass of a metal oxide produced by adjusting the mass of the starting materials added such that the composition of the metal oxide is made to be $Mo_{12}Bi_{0.39}Fe_{1.60}CO_{4.30}Ni_{3.45}Ce_{0.68}Rb_{0.16}O_f$ is carried on 42% by mass of silica was produced according to the following procedure.

First, to 1400 g of silica sol containing 30% by mass of $SiO_2$ having an average particle diameter of primary particles of 12 nm, 25.0 g of oxalic acid dihydrate dissolved in 200 g of water was added, and 465.5 g of ammonium paramolybdate $[(NH_4)_6Mo_7O_{24}\cdot 4H_2O]$ dissolved in 836.85 g of water was added under stirring to obtain a mixed liquid containing molybdenum and silica. Hereafter, this is referred to as A3 liquid. The whole amount of the A3 liquid was 2927 g.

Next, in 394.5 g of 16.6% by mass of nitric acid, 36.1 g of bismuth nitrate $[Bi(NO_3)_3\cdot 5H_2O]$, 141.6 g of iron nitrate $[Fe(NO_3)_3\cdot 9H_2O]$, 275.1 g of cobalt nitrate $[Co(NO_3)_2\cdot 6H_2O]$, 219.9 g of nickel nitrate $[Ni(NO_3)_2\cdot 6H_2O]$, 64.6 g of cerium nitrate $[Ce(NO_3)_3\cdot 6H_2O]$, and 5.33 g of rubidium nitrate $[RbNO_3]$ were dissolved. Hereafter, this is referred to as B3 liquid. The whole amount of the B3 liquid was 1137 g.

In the same manner as in Example 32, the A3 liquid held at 40° C. and the B3 liquid held at 40° C. were contacted with each other in the same manner as in Example 32 at a flow rate of 292 (g/min) and at a flow rate of 115 (g/min), respectively. This operation was conducted for 10 minutes to prepare a MoBi-containing liquid being a slurry. The supply ratio of the B3 liquid [Bi-containing liquid] to the A3 liquid [Mo-containing liquid] during this operation was 115 (g/min)/292 (g/min)=0.39, which was 1.0 times the mass ratio of the whole amount of the Bi-containing liquid to the whole amount of the Mo-containing liquid, 1137 (g)/2927 (g)=0.39. All (100% by mass) of the A3 liquid and the B3 liquid were merged at this supply ratio. The merging temperature during the operation was 40° C.

The whole amount of this MoBi-containing liquid was stored in the slurry-stirring tank provided at downstream from the stationary type mixer, and stirring was further continued at 40° C. for 1 hour after supplying the two liquids was completed. This MoBi-containing liquid had a pH of 1 or less and was in the form of a slurry before spray-drying. Subsequently, this MoBi-containing liquid was spray-dried in the same manner as in Example 32 to obtain a dried powder. It is to be noted that the hot-air inlet temperature was set to 230° C., and the hot-air outlet temperature was set to 110° C.

Subsequently, preliminary calcination was applied to the dried catalyst precursor using an electric furnace such that the dried catalyst precursor was held at 200° C. for 5 minutes in an air atmosphere, the temperature was then raised from 200° C. to 450° C. at 2.5° C./min, and the dried catalyst precursor was then held at 450° C. for 20 minutes, and thereafter final calcination was applied at 585° C. for 2 hours in an air atmosphere to obtain a catalyst (catalyst 3).

The standard deviation value of the catalyst 3 obtained in the same manner as in Example 32 and the results of the ammoxidation reaction are shown in Table 4.

Example 35

[Production of Catalyst 4]

A Mo-containing liquid (the same as A1 liquid; however, hereafter, referred to as "A4 liquid") and a Bi-containing liquid (the same as B1 liquid; however, hereafter, referred to as "B4 liquid") were prepared in the same manner as in Example 1. The whole amount of supplied A4 liquid and of supplied B4 liquid were the same as those in Example 32, and accordingly, the mass ratio in this case was 0.42, which was the same as the mass ratio in Example 32.

A catalyst (catalyst 4) was obtained in the same manner as in Example 32 except that the supply ratio of the B4 liquid to the A4 liquid was varied between 0.8 times to 1.2 times the mass ratio of 0.42. All (100% by mass) of the A4 liquid and the B4 liquid were merged at supply ratios in this range.

Specifically, merging was performed as follows. The A4 liquid and the B4 liquid were simultaneously supplied to the Y-shaped pipe at a flow rate of 302 (g/min) through the first flow channel and at a flow rate of 102 (g/min) through the second flow channel, respectively, for 3 minutes. This supply ratio was 102 (g/min)/302 (g/min)=0.34 and 0.8 times the mass ratio of 0.42.

Next, the flow rate of the A4 liquid supplied and of the B4 liquid supplied were changed, and the A4 liquid and the B4 liquid were simultaneously supplied at a flow rate of 284 (g/min) and at a flow rate of 120 (g/min), respectively, for 4 minutes. The supply ratio on that occasion was 120 (g/min)/284 (g/min)=0.42 and 1.0 times the mass ratio of 0.42.

Further, the flow rate of the A4 liquid supplied and of the B4 liquid supplied were changed, and the A4 liquid and the B4 liquid were simultaneously supplied at a flow rate of 268 (g/min) and at a flow rate of 136 (g/min), respectively, for 3 minutes. The supply ratio on that occasion was 136 (g/min)/268 (g/min)=0.51 and 1.2 times the mass ratio of 0.42.

It is to be noted that the merging temperature of the A4 liquid and the B4 liquid was 40° C. at any stage. The produced MoBi-containing liquid had a pH of 1 or less and was in the form of a slurry before spray-drying.

The standard deviation value of the catalyst 4 obtained in the same manner as in Example 32 and the results of the ammoxidation reaction are shown in Table 4.

Example 36

[Production of Catalyst 5]

A Mo-containing liquid (the same as A1 liquid; however, hereafter, referred to as "A5 liquid") and a Bi-containing liquid (the same as B1 liquid; however, hereafter, referred to as "B5 liquid") were prepared in the same manner as in Example 32. The whole amount of supplied A5 liquid and of supplied B5 liquid were the same as those in Example 32, and accordingly, the mass ratio in this case was 0.42, which was the same as the mass ratio in Example 32.

A catalyst (catalyst 5) was obtained in the same manner as in Example 32 except that the supply ratio of the B5 liquid to the A5 liquid was varied between 0.5 times to 1.5 times the mass ratio of 0.42. All (100% by mass) of the A5 liquid and the B5 liquid were merged at supply ratios in this range.

Specifically, merging was performed as follows. The A5 liquid and the B5 liquid were simultaneously supplied to the Y-shaped pipe at a flow rate of 334 (g/min) and at a flow rate of 70 (g/min), respectively, for 3 minutes. This supply ratio was 70 (g/min)/334 (g/min)=0.21 and 0.5 times the mass ratio of 0.42.

Next, the flow rate of the A5 liquid supplied and of the B5 liquid supplied were changed, and the A5 liquid and the B5 liquid were simultaneously supplied at a flow rate of 284 (g/min) and at a flow rate of 120 (g/min), respectively, for 5 minutes. This supply ratio was 120 (g/min)/284 (g/min)=0.42 and 1.0 times the mass ratio of 0.42.

Further, the flow rate of the A5 liquid supplied and of the B5 liquid supplied were changed, and the A5 liquid and the B5 liquid were simultaneously supplied at a flow rate of 248 (g/min) and at a flow rate of 156 (g/min), respectively, for 2 minutes. This supply ratio was 156 (g/min)/248 (g/min)=0.63 and 1.5 times the mass ratio of 0.42. It is to be noted that the merging temperature of the A5 liquid and the B5 liquid was 40° C. at any stage. The produced MoBi-containing liquid had a pH of 1 or less and was in the form of a liquid before spray-drying.

The standard deviation value of the catalyst 5 obtained in the same manner as in Example 32 and the results of the ammoxidation reaction are shown in Table 4.

Example 37

[Production of Catalyst 6]

A catalyst (catalyst 6) was obtained in the same manner as in Example 32 except that the Mo-containing liquid and the Bi-containing liquid were directly fed to the spray drier without being temporarily stored in the slurry-stirring tank after being mixed in the Y-shaped pipe and the stationary type mixer. It is to be noted that the merging temperature was 40° C. The produced MoBi-containing liquid had a pH of 1 or less and was in the form of a slurry before spray-drying.

The standard deviation value of the catalyst 6 obtained in the same manner as in Example 32 and the results of ammoxidation reaction are shown in Table 4.

Example 38

[Production of Catalyst 7]

A Mo-containing liquid (the same as A1 liquid; however, hereafter, referred to as "A7 liquid") and a Bi-containing liquid (the same as B1 liquid; however, hereafter, referred to as "B7 liquid") were prepared in the same manner as in Example 32. The mass ratio in this case was 0.42, which was the same as the mass ratio in Example 32.

Merging was performed such that the supply ratio of the B7 liquid to the A7 liquid was within the range of 0.5 times to 1.5 times the mass ratio of 0.36 for the amount corresponding to 60% by mass of the total amount of the whole amounts of the Mo-containing liquid and the Bi-containing liquid supplied. Merging was performed such that the supply ratio was out of the range of 0.5 times to 1.5 times for the remaining 40% by mass. A catalyst (catalyst 7) was produced in the same manner as in Example 32 except for those described above.

Specifically, merging was performed as follows. Supply of the A7 liquid at a flow rate of 334 (g/min) and supply of the B7 liquid at a flow rate of 70 (g/min) were simultaneously started to the Y-shaped pipe through piping and continued for 2 minutes. The supply ratio on that occasion was 70 (g/min)/334 (g/min)=0.21, which was 0.5 times the mass ratio of 0.42.

Next, the flow rate of the A7 liquid supplied and of the B7 liquid supplied were changed, and the A7 liquid and the B7 liquid were simultaneously supplied at a flow rate of 229 (g/min) and at a flow rate of 192 (g/min), respectively, for 2 minutes. The supply ratio on that occasion was 192 (g/min)/229 (g/min)=0.84, which was 2.0 times the mass ratio of 0.42.

Further, the flow rate of the A7 liquid supplied and of the B7 liquid supplied were changed, and the A7 liquid and the B7 liquid were simultaneously supplied at a flow rate of 284 (g/min) and at a flow rate of 119 (g/min), respectively, for 2 minutes. The supply ratio on that occasion was 119 (g/min)/284 (g/min)=0.42, which was 1.0 times the mass ratio of 0.42.

Subsequently, the flow rate of the A7 liquid supplied and of the B7 liquid supplied were changed, and the A7 liquid and the B7 liquid were simultaneously supplied at a flow rate of 356 (g/min) and at a flow rate of 45 (g/min), respectively, for 2 minutes. The supply ratio on that occasion was 45 (g/min)/356 (g/min)=0.13, which was 0.3 times the mass ratio of 0.42.

Finally, the flow rate of the A7 liquid supplied and of the B7 liquid supplied were changed, and the A7 liquid and the B7 liquid were simultaneously supplied at a flow rate of 248 (g/min) and at a flow rate of 156 (g/min), respectively, for 2 minutes. The supply ratio on that occasion was 156 (g/min)/248 (g/min)=0.63, which was 1.5 times the mass ratio of 0.42.

It is to be noted that the merging temperature of the A7 liquid and the B7 liquid was 40° C. at any stage.

After that, a catalyst (catalyst 7) was obtained in the same manner as in Example 32. This MoBi-containing liquid had a pH of 1 or less and was in the form of a slurry before spray-drying.

The standard deviation value of the catalyst 7 obtained in the same manner as in Example 32 and the results of the ammoxidation reaction are shown in Table 4.

Reference Example 1

[Production of Catalyst 8]

A Mo-containing liquid (the same as A1 liquid; however, hereafter, referred to as "A8 liquid") and a Bi-containing liquid (the same as B1 liquid; however, hereafter, referred to as "B8 liquid") were prepared in the same manner as in Example 32.

The B8 liquid held at 40° C. was put into the A8 liquid held at 40° C. while performing stirring to prepare a MoBi-containing liquid. A quantitative liquid feeding pump was used for putting in the liquid.

Specifically, 1198 g of the B8 liquid was supplied at a flow rate of 599 (g/min) to 2843 g, the whole amount, of the A8 liquid. The produced MoBi-containing liquid was further stirred at 40° C. for 1 hour. This MoBi-containing liquid had a pH of 1 or less and was in the form of a slurry before spray-drying.

After that, a catalyst (catalyst 8) was obtained in the same manner as in Example 32.

The standard deviation value of the catalyst 8 obtained in the same manner as in Example 32 and the results of the ammoxidation reaction are shown in Table 4.

Reference Example 2

[Production of Catalyst 9]

A Mo-containing liquid (the same as A1 liquid; however, hereafter, referred to as "A9 liquid") and a Bi-containing liquid (the same as B1 liquid; however, hereafter, referred to as "B9 liquid") were prepared in the same manner as in Example 32.

The A9 liquid held at 40° C. was put into the B9 liquid held at 40° C. while performing stirring to prepare a MoBi-containing liquid. A quantitative liquid feeding pump was used for putting in the liquid.

Specifically, 2843 g of the A9 liquid was supplied at a flow rate of 1422 (g/min) to 1198 g, the whole amount, of the B9 liquid. The produced MoBi-containing liquid was further stirred at 40° C. for 1 hour. This MoBi-containing liquid had a pH of 1 or less and was in the form of a slurry before spray-drying.

After that, a catalyst (catalyst 9) was obtained in the same manner as in Example 32.

The standard deviation value of the catalyst 9 obtained in the same manner as in Example 32 and the results of the ammoxidation reaction are shown in Table 4.

(Production Conditions and Yield of Acrylonitrile Through Ammoxidation Reaction of Propylene)

The yield of acrylonitrile produced through the reaction was calculated based on the above-described evaluation method.

(Evaluation of Uniformity of Composition on Surface of Catalyst Particle)

The evaluation of the uniformity of the composition on the surface of the catalyst particles in Examples and Reference Examples was performed as follows and is expressed as the standard deviation of the composition on the surface of the catalyst particles.

On a specimen stage of a SEM-EDX (Scanning Electron Microscopes-Energy Dispersive X-ray Spectroscopy) composition analysis apparatus (SEM . . . manufactured by Hitachi, Ltd., model: SU-70, EDX . . . manufactured by HORIBA, Ltd., model: EMAX•X-max), a small amount of a metal oxide particle (calcined particle) was taken, and the molar concentration of Mo and the molar concentration of Bi in the range of a face of 10 μm×10 μm on the surface of each particle were measured (magnification of 1500 times, acceleration voltage of 20 kV) for 100 particles each having an equivalent circle diameter (diameter of a circle the area of which is equivalent to the area of an image of a particle) in an image of particles randomly selected of an average particle diameter±10 μm, the average particle diameter decided with a laser diffraction/scattering type particle size distribution measurement apparatus (laser diffraction/scattering type particle size distribution measurement apparatus LA-300 manufactured by HORIBA, Ltd.) to determine the ratio of the concentration of Bi to the concentration of Mo, (Bi/Mo), on the surface of the particles.

Next, 20 mg of a specimen was weighed from the same catalyst powder, dissolved with hot aqua regia of 210° C., and further, diluted with ultrapure water to a measurement range to measure the concentration of each constituent element by ICP atomic emission spectrophotometry (manufactured by Seiko Instruments Inc., SPS3500DD), and thus the bulk composition of the metal oxide contained in the catalyst was calculated, and the ratio of the concentration of Bi to the concentration of Mo of the metal oxide, $(Bi/Mo)_{bulk}$, was determined. It is to be noted that in the catalysts 1 to 9, which will be described later, any of the bulk compositions of the metal oxides agreed with the theoretical value calculated from the mass of the starting materials added (the same to the second highest digit as the molar composition calculated from the mass of the starting materials added in the molar composition represented on $Mo_{12}$ basis)

A value obtained by dividing the above-described $(Bi/Mo)_{surf}$ of each of 100 particles by this $(Bi/Mo)_{bulk}$ is denoted as $S_k$ (k=1 to 100), and the average value μ of 100 $S_k$s is calculated to determine the standard deviation from formula (4).

$$\text{Standard deviation} = \{((S_1-\mu)^2+(S_2-\mu)^2+\ldots+(S_{100}-\mu)^2)/100[\text{Number}]\}^{1/2} \quad (4)$$

The bulk composition of each metal oxide contained in the catalysts obtained in Examples and Reference Examples is shown in Table 3, and the standard deviation of $(Bi/Mo)_{surf}/(Bi/Mo)_{bulk}$ on the surface of the catalyst particles is shown in Table 4. Further, production conditions for each catalyst and the yield in producing acrylonitrile using each catalyst are also shown in Table 4.

It is to be noted that the bulk compositions of the metal oxides contained in the catalysts obtained in Examples 32 and 35 to 38, and Reference Examples 1 to 2 were the same.

*1: Merging was performed within a range where the supply ratio is 0.5 times to 1.5 times the mass ratio for 60% by mass of the whole amount of the Mo-containing liquid and the Bi-containing liquid supplied and within a range other than that for the remaining 40% by mass thereof.

In Examples 32 to 38 where a catalyst was produced using a MoBi-containing liquid prepared by merging a Mo-containing liquid and a Bi-containing liquid supplied to the first and the second flow channels, respectively, at a merging section, a catalyst in which the composition ratio between Mo and Bi on the surface of the catalyst particle is uniform can be continuously produced. In addition, in the cases where the catalyst produced in these Examples was used, acrylonitrile can be produced at a higher yield.

On the other hand, in Reference Example 1 where the Bi-containing liquid was put into the Mo-containing liquid (whole amount) and Reference Example 2 where the Mo-containing liquid was put into the Bi-containing liquid (whole amount), the uniformity of the composition ratio between Mo and Bi on the surface of the resultant catalyst particle was lower than that in Examples 32 to 38. In addition, the yield of acrylonitrile in the cases where the catalysts obtained in Reference Examples 1 and 2 were used was lower than that in Examples 32 to 38.

From those described above, it was confirmed that the more uniform the surface composition of a catalyst particle is (that is, the smaller the standard deviation is), the higher acrylonitrile yield (catalyst performance) is exhibited in a reaction in which acrylonitrile is produced through ammoxidation reaction of propylene.

TABLE 3

|  | Catalyst | Mo | Bi | Fe | Ni | Co | Mg | Ce | Cr | Rb | Amount of $SiO_2$ carrier wt % |
|---|---|---|---|---|---|---|---|---|---|---|---|
| Example 32 | 1 | 12 | 0.25 | 1.4 | 3.0 | 5.8 | — | 0.40 | 0 | 0.12 | 40 |
| Example 33 | 2 | 12 | 0.39 | 1.6 | 7.0 | — | 0.77 | 0.63 | 0 | 0.17 | 40 |
| Example 34 | 3 | 12 | 0.34 | 1.6 | 3.5 | 4.3 | — | 0.68 | 0 | 0.16 | 42 |
| Example 35 | 4 | 12 | 0.25 | 1.4 | 3.0 | 5.8 | — | 0.40 | 0 | 0.12 | 40 |
| Example 36 | 5 | 12 | 0.25 | 1.4 | 3.0 | 5.8 | — | 0.40 | 0 | 0.12 | 40 |
| Example 37 | 6 | 12 | 0.25 | 1.4 | 3.0 | 5.8 | — | 0.40 | 0 | 0.12 | 40 |
| Example 38 | 7 | 12 | 0.25 | 1.4 | 3.0 | 5.8 | — | 0.40 | 0 | 0.12 | 40 |
| Reference Example 1 | 8 | 12 | 0.25 | 1.4 | 3.0 | 5.8 | — | 0.40 | 0 | 0.12 | 40 |
| Reference Example 2 | 9 | 12 | 0.25 | 1.4 | 3.0 | 5.8 | — | 0.40 | 0 | 0.12 | 40 |

TABLE 4

|  | Catalyst | Supply ratio/mass ratio | Merging angle | (v) step | Standard deviation value | Conversion rate of propylene [%] | Acrylonitrile yield [%] |
|---|---|---|---|---|---|---|---|
| Example 32 | 1 | 1.0 | Parallel | Performed | 0.04 | 99.2 | 84.5 |
| Example 33 | 2 | 1.0 | Parallel | Performed | 0.03 | 99.2 | 84.3 |
| Example 34 | 3 | 1.0 | Parallel | Performed | 0.07 | 99.4 | 84.6 |
| Example 35 | 4 | 0.8~1.2 | Parallel | Performed | 0.06 | 99.3 | 84.4 |
| Example 36 | 5 | 0.5~1.5 | Parallel | Performed | 0.07 | 99.3 | 84.4 |
| Example 37 | 6 | 1.0 | Parallel | Not performed | 0.09 | 99.2 | 84.3 |
| Example 38 | 7 | 0.5~1.5[*1] | Parallel | Performed | 0.18 | 99.2 | 84.3 |
| Reference Example 1 | 8 | — | — | Performed | 0.23 | 99.2 | 84.0 |
| Reference Example 2 | 9 | — | — | Performed | 0.31 | 99.2 | 83.7 |

INDUSTRIAL APPLICABILITY

The method for producing a catalyst according to the present invention has industrial applicability as a method for producing a catalyst to be used for ammoxidation reaction of propylene.

The invention claimed is:

1. A method for producing a catalyst, comprising:
    a preparation step of preparing a precursor slurry comprising molybdenum, bismuth, iron, silica, and a carboxylic acid;
    a drying step of spray-drying the precursor slurry and thereby obtaining a dried particle; and
    a calcination step of calcining the dried particle, wherein the preparation step comprises:
    a step (I) of mixing a starting material for silica with the carboxylic acid and thereby preparing a silica-carboxylic acid mixed liquid; and
    a step (II) of mixing the silica-carboxylic acid mixed liquid, molybdenum, bismuth, and iron.

2. The method for producing the catalyst according to claim 1, wherein the catalyst comprises:
    a metal oxide having a bulk composition represented by the following formula (1); and
    silica:

$$Mo_{12}Bi_aFe_bX_cY_dZ_eO_f \qquad (1)$$

wherein X represents at least one element selected from the group consisting of nickel, cobalt, magnesium, calcium, zinc, strontium, and barium; Y represents at least one element selected from the group consisting of cerium, chromium, lanthanum, neodymium, yttrium, praseodymium, samarium, aluminum, gallium, and indium; Z represents at least one element selected from the group consisting of potassium, rubidium, and cesium; a, b, c, d, e and f represent an atomic ratio of each element, and satisfy $0.1 \leq a \leq 3.0$, $0.1 \leq b \leq 3.0$, $0.1 \leq c \leq 10.0$, $0.1 \leq d \leq 3.0$, and $0.01 \leq e \leq 2.0$, respectively, and f represents a number of oxygen atoms needed to satisfy atomic valence requirements of the other elements present therein.

3. The method for producing the catalyst according to claim 2, wherein in the catalyst, a standard deviation of values obtained by dividing a ratio of a molar concentration of Bi to a molar concentration of Mo on a surface of catalyst particles by a ratio of a molar concentration of Bi to a molar concentration of Mo in a metal oxide bulk is 0.2 or less.

4. The method for producing the catalyst according to claim 1, wherein
    the step (II) comprises the following (i) step and (ii) step, and
    the drying step comprises the following (iii) step;
    (i) a step of preparing a Mo-containing liquid comprising at least Mo and a Bi-containing liquid comprising at least Bi,
    (ii) a step of continuously supplying the Mo-containing liquid to a first flow channel, continuously supplying the Bi-containing liquid to a second flow channel, and merging the first flow channel and the second flow channel at downstream from both points of supply of the Mo-containing liquid and the Bi-containing liquid, and consequently mixing the Mo-containing liquid and the Bi-containing liquid to thereby obtain a MoBi-containing liquid, and
    (iii) a step of drying the MoBi-containing liquid.

5. The method for producing the catalyst according to claim 4, further comprising (iv) a step of further mixing the MoBi-containing liquid performed between the (ii) step and the (iii) step.

6. The method for producing the catalyst according to claim 4, further comprising (v) a step of storing the MoBi-containing liquid performed between the (ii) step and the (iii) step.

7. The method for producing the catalyst according to claim 6,
    wherein a series of treatments of the (i), (ii), and (v) steps is performed in a batch treatment methodology, and a whole amount of one batch of the MoBi-containing liquid obtained in the (ii) step is stored in the (v) step; and
    in the (ii) step, when mass supply rates of the Mo-containing liquid and the Bi-containing liquid to the first flow channel and the second flow channel, respectively, are denoted as mA (g/min) and mB (g/min), respectively, 60% by mass or more of a total amount of whole amounts of the Mo-containing liquid and the Bi-containing liquid supplied per batch, MA (g) and MB (g), respectively, is supplied such that the following formula (2) is satisfied:

$$(mB/mA)/(MB/MA)=0.5 \text{ to } 1.5 \qquad (2).$$

8. The method for producing the catalyst according to claim 4, wherein the MoBi-containing liquid is continuously supplied to the (iii) step.

9. The method for producing the catalyst according to claim 4, wherein in the (ii) step, when molar supply rates of the Mo-containing liquid and the Bi-containing liquid to the first flow channel and the second flow channel, respectively, are denoted as mα (mol/min) and mβ (mol/min), respectively, the Mo-containing liquid and the Bi-containing liquid are supplied such that the following formula (3) is satisfied:

$$(m\beta/m\alpha)/(a/12)=0.8 \text{ to } 1.2 \qquad (3).$$

10. A method for producing acrylonitrile, comprising:
    a step of obtaining the catalyst by the method for producing the catalyst according to claim 1; and
    a step of reacting propylene, molecular oxygen, and ammonia in a presence of the catalyst.

11. A catalyst comprising a particle, the particle comprising:
    a metal oxide having a bulk composition represented by the following formula (1); and
    silica,
    wherein a standard deviation of values obtained by dividing a ratio of a molar concentration of Bi to a molar concentration of Mo on a surface of the catalyst particles by a ratio of a molar concentration of Bi to a molar concentration of Mo in a metal oxide bulk is 0.2 or less:

$$Mo_{12}Bi_aFe_bX_cY_dZ_eO_f \qquad (1)$$

wherein X represents at least one element selected from the group consisting of nickel, cobalt, magnesium, calcium, zinc, strontium, and barium; Y represents at least one element selected from the group consisting of cerium, chromium, lanthanum, neodymium, yttrium, praseodymium, samarium, aluminum, gallium, and indium; Z represents at least one element selected from the group consisting of potassium, rubidium, and cesium; a, b, c, d, e and f represent an atomic ratio of each element, and satisfy $0.1 \leq a \leq 3.0$, $0.1 \leq b \leq 3.0$, $0.1 \leq c \leq 10.0$, $0.1 \leq d \leq 3.0$, and $0.01 \leq e \leq 2.0$, respectively, and f represents a value satisfying a balance of atomic valences.

12. A method for producing acrylonitrile, comprising a step of reacting propylene, molecular oxygen, and ammonia in a presence of the catalyst according to claim 11.

* * * * *